(12) United States Patent
Gendreau et al.

(10) Patent No.: US 7,796,726 B1
(45) Date of Patent: Sep. 14, 2010

(54) INSTRUMENT AND METHOD FOR X-RAY DIFFRACTION, FLUORESCENCE, AND CRYSTAL TEXTURE ANALYSIS WITHOUT SAMPLE PREPARATION

(75) Inventors: Keith Gendreau, Greenbelt, MD (US); Jose Vanderlei Martins, Greenbelt, MD (US); Zaven Arzoumanian, Greenbelt, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 302 days.

(21) Appl. No.: 11/706,693

(22) Filed: Feb. 14, 2007

Related U.S. Application Data

(60) Provisional application No. 60/773,244, filed on Feb. 14, 2006, provisional application No. 60/776,576, filed on Feb. 24, 2006.

(51) Int. Cl.
G01N 23/223 (2006.01)
G01N 23/20 (2006.01)

(52) U.S. Cl. .............. 378/46; 378/44; 378/45; 378/49; 378/71; 378/76; 378/79; 378/80; 378/81; 378/82; 378/83

(58) Field of Classification Search .......... 378/44, 378/45, 46, 49, 70, 71, 72, 73, 75, 76, 79, 378/80, 81, 82, 83
See application file for complete search history.

(56) References Cited

U.S. PATENT DOCUMENTS

| | | | |
|---|---|---|---|
| 5,491,738 A | 2/1996 | Blake et al. | 378/71 |
| 5,832,054 A * | 11/1998 | Kuwabara | 378/45 |
| 5,978,442 A * | 11/1999 | Kuwabara | 378/46 |
| 6,163,592 A * | 12/2000 | He et al. | 378/71 |
| 6,173,037 B1 * | 1/2001 | Brouwer | 378/45 |
| 6,233,307 B1 * | 5/2001 | Golenhofen | 378/45 |
| 6,295,333 B1 * | 9/2001 | Tamura | 378/44 |
| 6,359,962 B1 * | 3/2002 | Yagi | 378/44 |
| 6,370,220 B1 * | 4/2002 | Stoop | 378/45 |
| 6,400,795 B2 * | 6/2002 | Yagi | 378/45 |
| 6,577,705 B1 * | 6/2003 | Chang et al. | 378/45 |
| 6,661,876 B2 * | 12/2003 | Turner et al. | 378/138 |
| 6,718,008 B1 * | 4/2004 | He et al. | 378/71 |
| 6,751,287 B1 * | 6/2004 | Kalyon et al. | 378/71 |
| 6,798,863 B2 * | 9/2004 | Sato | 378/46 |
| 6,836,532 B2 * | 12/2004 | Durst et al. | 378/73 |
| 7,245,696 B2 * | 7/2007 | Yun et al. | 378/45 |

(Continued)

OTHER PUBLICATIONS

B. D. Cullity and S. R. Stock, Elements of X-Ray Diffraction, third edition (New Jersey: Prentice-Hall, 2001), p. 216-217.*

*Primary Examiner*—Allen C. Ho
(74) *Attorney, Agent, or Firm*—Nixon Peabody LLP

(57) ABSTRACT

An X-ray diffraction and X-ray fluorescence instrument for analyzing samples having no sample preparation includes a X-ray source configured to output a collimated X-ray beam comprising a continuum spectrum of X-rays to a predetermined coordinate and a photon-counting X-ray imaging spectrometer disposed to receive X-rays output from an unprepared sample disposed at the predetermined coordinate upon exposure of the unprepared sample to the collimated X-ray beam. The X-ray source and the photon-counting X-ray imaging spectrometer are arranged in a reflection geometry relative to the predetermined coordinate.

15 Claims, 22 Drawing Sheets
(8 of 22 Drawing Sheet(s) Filed in Color)

U.S. PATENT DOCUMENTS 7,321,652 B2 * 1/2008 Yokhin et al. .................. 378/82
7,430,273 B2 * 9/2008 Yellepeddi ................... 378/44
7,443,951 B2 * 10/2008 Kenning et al. ............... 378/44

* cited by examiner

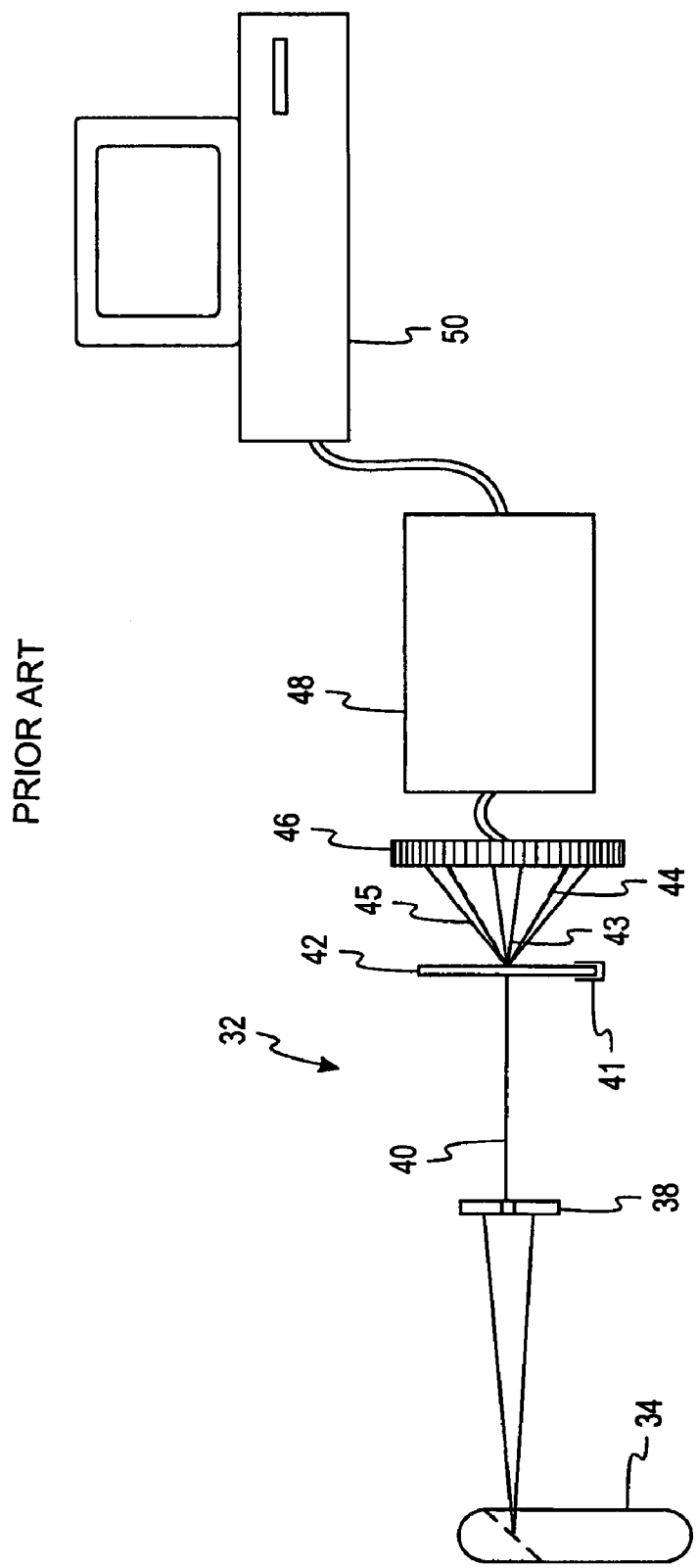

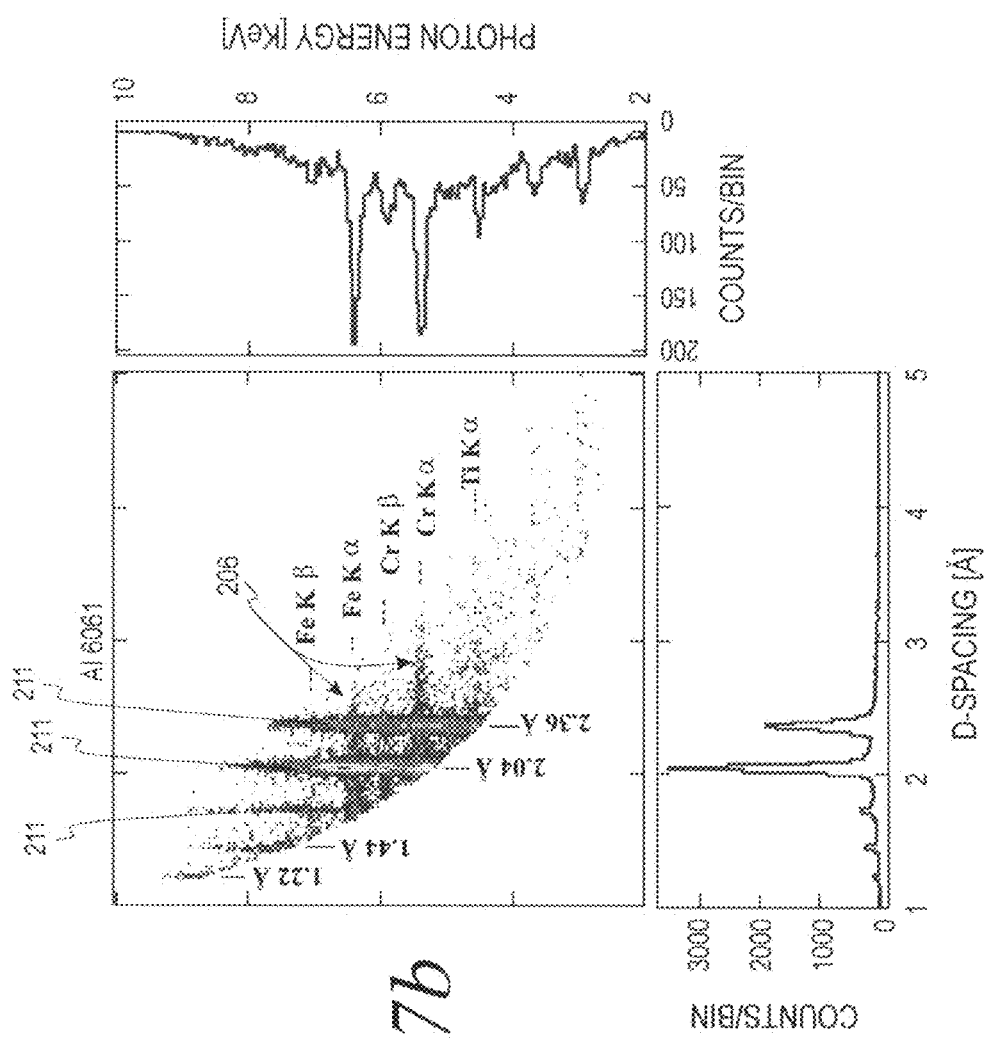

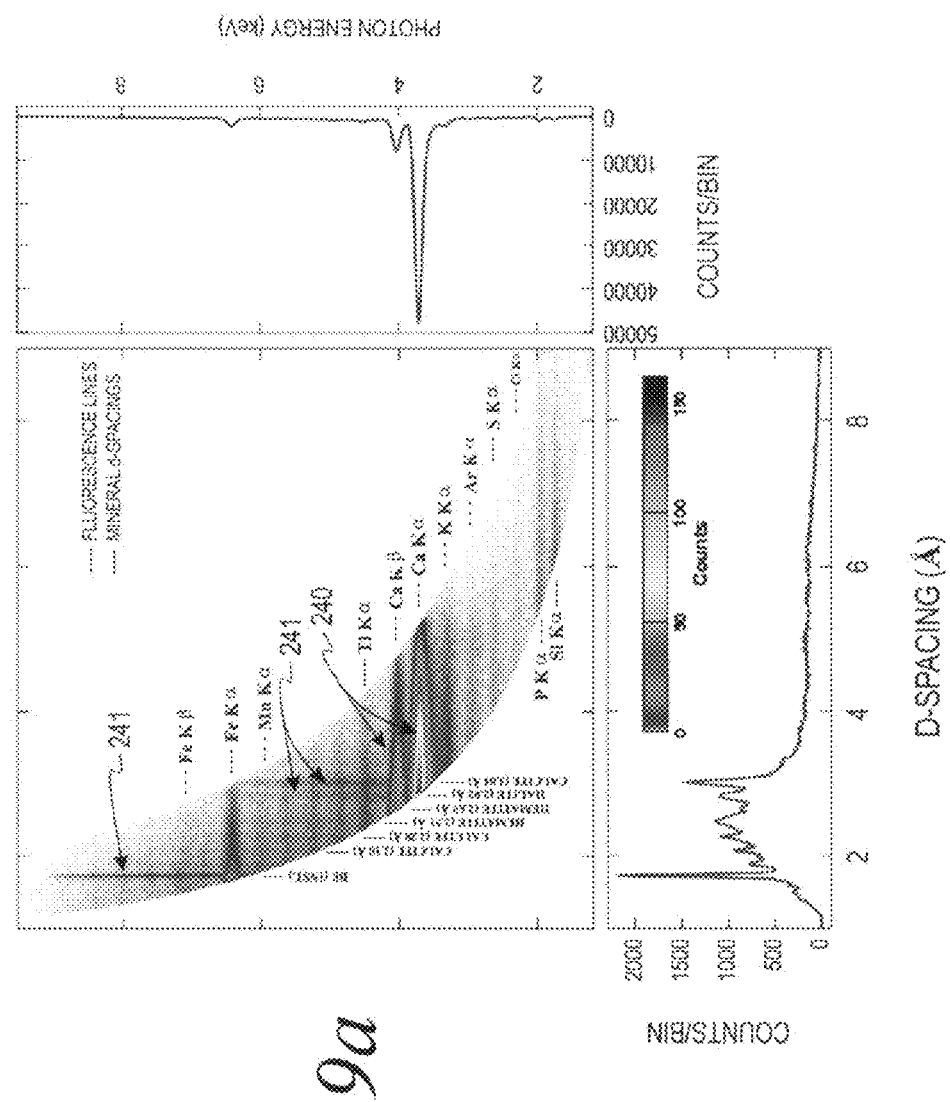

INSTRUMENT AND METHOD FOR X-RAY DIFFRACTION, FLUORESCENCE, AND CRYSTAL TEXTURE ANALYSIS WITHOUT SAMPLE PREPARATION

CROSS-REFERENCE TO RELATED APPLICATION

This application claims the benefit of the U.S. Provisional Patent Application No. 60/773,244 filed on Feb. 14, 2006 and entitled "Instrument And Method For X-ray Diffraction, Fluorescence, And Crystal Texture Analysis Without Sample Preparation" and U.S. Provisional Application No. 60/776,576 filed on Feb. 24, 2006 and entitled "Instrument And Method For X-ray Diffraction, Fluorescence, And Crystal Texture Analysis Without Sample Preparation" and each of these provisional patent applications is hereby incorporated by reference in its entirety.

RELATED APPLICATIONS

The invention described herein was made in the performance of work under a NASA contract or grant and by employees of the United States Government and is subject to the provisions of Section 305 of the National Aeronautics and Space Act of 1958, as amended, Public Law 85-568 (72 Stat. 435, 42 USC 2457) and may be manufactured and used by or for the Government for governmental purposes without the payment of any royalties thereon or therefor. The NASA grant numbers are NNG-05-CQ-79-A, NCC5-637 and RSP-0269-0154.

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present concepts relate generally to X-ray diffraction and X-ray fluorescence devices and methods of analyses of material data produced thereby.

BACKGROUND OF THE INVENTION

It is often the case that various material samples need to be analyzed for (1) identification of elemental composition, molecular makeup, or mineral content, (2) study of crystallization (e.g., in the study of food shelf lives), (3) evidence of stress and shock, (4) crystallite size and orientation distributions (i.e., crystalline texture). X-ray diffraction (XRD) is one of the primary techniques used by mineralogists and solid state chemists to examine various physical and chemical properties of unknown solids.

FIG. 1 shows a schematic representation of one conventional x-ray diffraction/x-ray fluorescence (XRD/XRF) instrument designed to characterize elemental composition and mineralogy from small fine-grained or powdered samples. This XRD apparatus 32, dubbed "CHEMIN" or "CheMin" due to its ability to provide a combined CHEmical and MINeralogical analysis, is disclosed in U.S. Pat. No. 5,491,738 to Blake et al. CheMin is one embodiment of the invention described in Blake et al.

The XRD apparatus 32 of FIG. 1 was designed to analyze x-ray diffraction pattern(s) from a thin-film sample 42 disposed in a sample holder 41. The sample has a sample thickness that allows production of diffracted x-rays at the back side of the sample (e.g., a transmissive Laue method) when the thin-film sample 42 is irradiated with beam 40. An x-ray emitter 34, such as a $CuK_\alpha$ emitter, is used to produce a broad spectrum of x-ray energies in a non-collimated beam. The non-collimated beam is passed through a collimator 38 to produce a collimated beam 40. The x-rays that are transmitted through the thin-film sample 42 are, in turn, incident upon a charge-coupled device (CCD) 46 containing a 2-dimensional planar array of pixels. The CCD 46 is an array detector adapted to record the energy of and position of individual incident X-rays.

Primary and secondary X-rays produced by irradiation of the sample 42 are directed onto the pixel array of the CCD 46. FIG. 1 shows three different diffraction cones 43, 44, and 45, which are due to diffraction from different-energy x-rays in the beam. A controller unit 48 is provided to receive input signals from each of the pixels in the CCD 46, relating to the pixel position and photon energy measured at each pixel, for use in constructing the diffraction pattern of photons within a selected energy range striking the array. A microprocessor 50 is used to provide a screen display for the controller unit and to permit control of the CCD settings by a user.

During irradiation, only a small region (e.g., 50 μm in diameter) is illuminated by the collimated X-ray beam 40. Following an exposure and data collection for a given substrate position, the thin-film sample 42 and/or x-ray emitter 34 is moved to a new position to expose another area of the thin-film sample 42. The x-rays are diffracted from the planes of atoms in the thin-film sample 42 into a spatial pattern on the CCD 46 that reveals the distribution of atoms in the sample. The spatial pattern of the diffracted X-rays detected by the CCD 46 is analyzed using Bragg's Law, which relates the wavelength (λ) of the X-ray, the atomic plane separation (d) of the sample, the diffracted angle (2θ) of the X-ray away from its original course, and the diffraction order (n) by the equation $n*\lambda=2*d*\sin(\theta)$. For a fixed wavelength (λ), the detector must span a large enough angle (θ), so that atomic plane separations (d) can be determined.

In conventional XRD techniques, such as that described above, a sample of a material of interest is powdered and placed on a thin-film substrate, which is then disposed in a holder. The sample is typically ground to a powder (e.g., less than 10 μm to about 100 μm) using a mill or mortar and pestle or the like. In certain applications (e.g., laboratory), samples may be prepared using acetone, isopropanol, pentane, or the like to form a uniform slurry, so as to minimize any potential problem with preferred orientation which may accompany rod-like or plate-like crystals. The prepared sample is then positioned within the XRD instrument and illuminated with x-rays, typically of a fixed wavelength, and the intensity of the diffracted radiation is recorded. The sample and/or x-ray source is then repositioned. Ideally, a large number of crystallites in random orientations are exposed to the X-ray beam, which is typically done by moving the specimen in the beam to analyze a larger number of crystallites and/or larger number of orientations of crystallites. This data is then analyzed for the diffraction angle to calculate the inter-atomic spacing (D) and the intensity (I) is measured to discriminate (using I ratios) the various D spacings and the results are used to identify possible matches when compared to known values (e.g., "The International Tables for Crystallography", the "International Center for Diffraction Data®" (ICDD) Powder Diffraction File™ covering over 550,000 compounds, etc.).

In still other conventional techniques, in single-crystal XRD, a goniometer is used to rotate a single crystal so that many facets and sets of atomic planes are oriented so as to diffract monochromatic rays onto a fixed detector. A pattern of diffraction spots ("Laue spots") results which, through traditional crystallographic algorithms, may be inverted to determine the underlying geometric arrangement of the atoms in the crystal.

However, conventional XRD/XRF instruments require either significant sample preparation and/or require the ability to reposition the instrument through a wide range of angles around the sample, or rotate the sample through a wide range of angles, so as to get desired sample information (e.g., identification of elemental compositions, identification of molecular makeup, identification of mineral content, study of crystallization, evidence of stress and/or shock in the material, crystal grain size, crystal orientation distributions, etc.). In either case, several moving parts are required to perform the XRD analysis. However, in certain applications, such as extraterrestrial XRD analysis, the number of moving parts required increases (e.g., the CheMin device uses a carousel disc and associated drive system, sample preparation systems such as a fine-grinding mill, etc.), with corresponding increases in power consumption, mass, and risk. For the CheMin XRD/XRF apparatus 32, which is presently slated for inclusion on the Mars Science Laboratory (MSL) mission scheduled for launch in 2009, sample preparation is required, which would disadvantageously destroy any water ice that MSL may encounter and cause it to evaporate in the low pressure environment on Mars. Sample preparation also destroys valuable scientific and engineering information regarding grain size and orientation distributions and evidence of stresses and shock.

SUMMARY OF THE INVENTION

In some aspects of the present concepts, an XRD/XRF instrument and method are provided which are particularly suited for extraterrestrial applications, such as may be used in combination with a rover, landing vehicle, or craft. Such a flight-instrument application requires that the instrument be robust, lightweight, and low in power consumption. In addition, risk must be minimized whenever possible. The XRD/XRF instrument presently disclosed herein, relative to conventional XRD/XRF instruments, eliminates moving parts, eliminates sample preparation needs, provides an efficient geometry, provides improved sensitivity, and eliminates the need to place samples in vacuum, each of which improvements decrease risk and, in combination, significantly decreases risks. Further, the XRD/XRF instrument and method provided herein should provide a platform for compact and rugged packaging that consumes a minimal amount of power. It is believed that a commercial XRD/XRF instrument based on the presently disclosed instrument and methods would cost significantly less than conventional XRD/XRF instruments.

In accord with disclosed aspects of the present concepts, an instrument and method for X-ray diffraction using a reflection geometry (and the methodology presented here; e.g. continuum X-ray source, and photon counting imaging spectrometer detectors) permit measuring the atomic plane spacings of unprepared material samples. The method described herein may alternatively be implemented in a transmission geometry. Further to providing material identification, the instrument(s) and method(s) permit the determination of the crystalline grain size, domain size, and orientation distributions (i.e., crystalline texture) within samples, which provide important information on crystallographic structure, material defects, and stresses or shocks that the sample may have experienced. The new method(s) described herein are very efficient compared to standard XRD techniques (including CheMin) for mineral and chemical identification. Further, the disclosed simultaneous X-ray fluorescence analysis capability provides elemental abundances.

According to one aspect of the present concepts an X-ray diffraction and X-ray fluorescence instrument for analyzing samples having no sample preparation includes a X-ray source configured to output a collimated X-ray beam comprising a continuum spectrum of X-rays to a predetermined coordinate and a photon-counting X-ray imaging spectrometer disposed to receive X-rays output from an unprepared sample disposed at the predetermined coordinate upon exposure of the unprepared sample to the collimated X-ray beam. The X-ray source and the photon-counting X-ray imaging spectrometer are arranged in a reflection geometry relative to the predetermined coordinate.

According to another aspect of the present concepts an X-ray diffraction and X-ray fluorescence instrument for analyzing samples, prepared or unprepared includes a X-ray source configured to output a collimated X-ray beam comprising a continuum spectrum of X-rays to a predetermined coordinate and a photon-counting X-ray imaging spectrometer disposed to receive X-rays output from the sample disposed at the predetermined coordinate upon exposure of the sample to the collimated X-ray beam. The X-ray source and the photon-counting X-ray imaging spectrometer are arranged in a reflection geometry relative to the predetermined coordinate.

According to another aspect of the invention, a method for performing X-ray diffraction and X-ray fluorescence on an unprepared sample includes the act of providing an X-ray diffraction and X-ray fluorescence instrument, comprising a broad-spectrum X-ray source and a photon-counting X-ray imaging spectrometer arranged in either a reflection geometry or a transmissive geometry relative to a predetermined coordinate position. The method also includes the acts of placing an unprepared sample at the predetermined coordinate position, outputting a collimated X-ray beam comprising a continuum spectrum of X-rays to the sample, and receiving, at the photon-counting X-ray imaging spectrometer, X-rays output from the sample upon exposure of the sample to the collimated X-ray beam. The method further includes outputting to a processor data corresponding to each X-ray photon registered by the photon-counting X-ray imaging spectrometer, preparing an event list, and analyzing, using the event list, a crystalline texture, crystalline topography, grain size, particle size, and/or time dependence of crystalline structure of the unprepared sample.

According to another aspect of the invention, a method for performing X-ray diffraction and X-ray fluorescence on a sample, whether prepared or unprepared, includes the act of providing an X-ray diffraction and X-ray fluorescence instrument, comprising a broad-spectrum X-ray source and a photon-counting X-ray imaging spectrometer arranged in either a reflection geometry or a transmissive geometry relative to a predetermined coordinate position. The method also includes the acts of placing a sample at the predetermined coordinate position, outputting a collimated X-ray beam comprising a continuum spectrum of X-rays to the sample, and receiving, at the photon-counting X-ray imaging spectrometer, X-rays output from the sample upon exposure of the sample to the collimated X-ray beam. The method further includes outputting to a processor data corresponding to each X-ray photon registered by the photon-counting X-ray imaging spectrometer, preparing an event list, and analyzing, using the event list, a crystalline texture, crystalline topography, grain size, particle size, and/or time dependence of crystalline structure of the sample.

According to still another aspect of the invention, an X-ray diffraction and X-ray fluorescence instrument for analyzing a prepared or an unprepared sample, comprises a X-ray source configured to output a collimated X-ray beam comprising a continuum spectrum of X-rays to a predetermined coordinate and a photon-counting X-ray imaging spectrometer. The photon-counting X-ray imaging spectrometer is disposed to receive X-ray photons output from the sample disposed at the predetermined coordinate upon exposure of the sample to the collimated X-ray beam. The X-ray source and the photon-counting X-ray imaging spectrometer being arranged in either a reflection geometry or a transmission geometry relative to the predetermined coordinate. This instrument also includes a processor and a computer-readable medium bearing instructions configured to cause the processor to carry out the steps of preparing an event list from information output to the processor by the photon-counting X-ray imaging spectrometer and analyzing, using the event list, a crystalline texture, crystalline topography, grain size, particle size, and/or time dependence of crystalline structure of the unprepared sample.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Objects and advantages of the invention will become apparent upon reading the following detailed description in conjunction with the drawings.

FIG. 1 is a schematic representation of a prior art X-ray diffraction apparatus.

FIGS. 7a-7e show results from an analysis of a bulk sample of aluminum-6061 obtained using a prototype XRD/XRF instrument in accord with at least some aspects of the present concepts.

FIGS. 9a-9c show data from an aerosol sample obtained using a prototype XRD/XRF instrument in accord with at least some aspects of the present concepts.

Figure 2A:
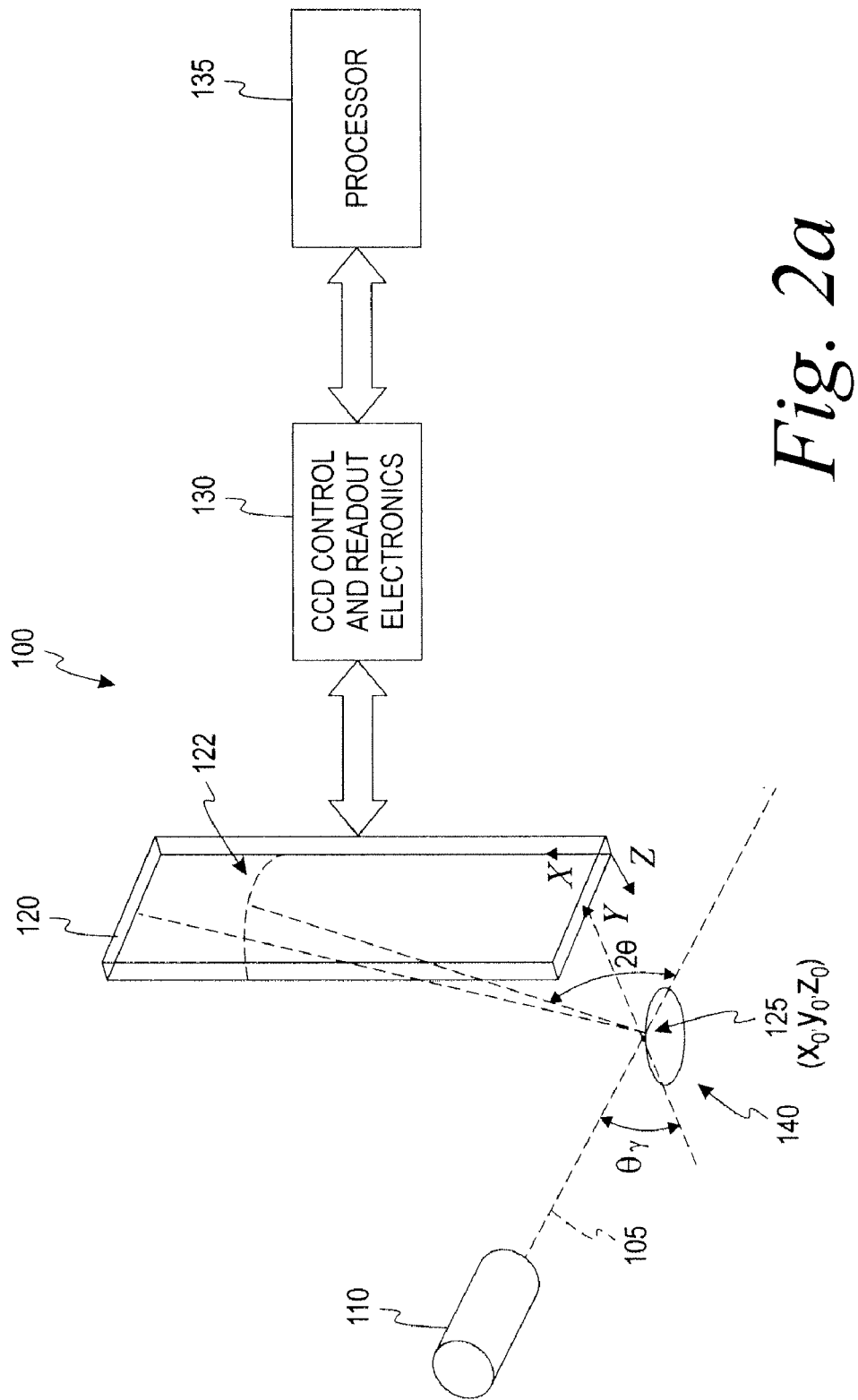
FIGS. 2a-2e show representations of aspects of embodiments of XRD/XRF devices in accord with aspects of the present concepts.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. The simplicity, size, weight, configuration, and performance of the apparatus disclosed herein facilitates optimization for and utilization in numerous applications including, but not limited to, manufacturing, scientific, mineralogy, gemological, food industry, pharmacology (e.g., pharmaceutical research, protein folding studies, etc.), medicine, life science, agriculture, agricultural science, law enforcement, defense, security, space, aerosols, and petrochemical applications (e.g., well logging). For example, it is envisaged that a XRD/XRF apparatus 100 in accord with aspects of the present concepts could be utilized as a flight-instrument on a mission to another planet, a planetary or celestial body, or an aircraft. In still other aspects, the XRD/XRF apparatus 100 may be implemented as a portable or even hand-held scanning device that may be used by researchers, police, soldiers, government personnel, engineers, mechanics, or other persons to gather data on objects, materials, or gases of interest. Thus, the presently disclosed XRD/XRF apparatus 100, as well as methods and techniques disclosed herein, may find application in numerous endeavors and are not limited to any of the disclosed examples.

Referring to FIGS. 2a-2e, the XRD/XRF apparatus 100 is shown to generally comprise a collimated, broad spectrum X-ray source 110 and a charge coupled device (CCD) 120 configured for X-ray detection arranged on opposite sides of a known sample position 125 (i.e., $x_0$, $y_0$, $z_0$), described below. The CCD 120 is positioned to receive X-ray photons 115, or other energy spectra, output (e.g., diffracted from, fluoresced from, etc.) from the sample 126.

Figure 2B:
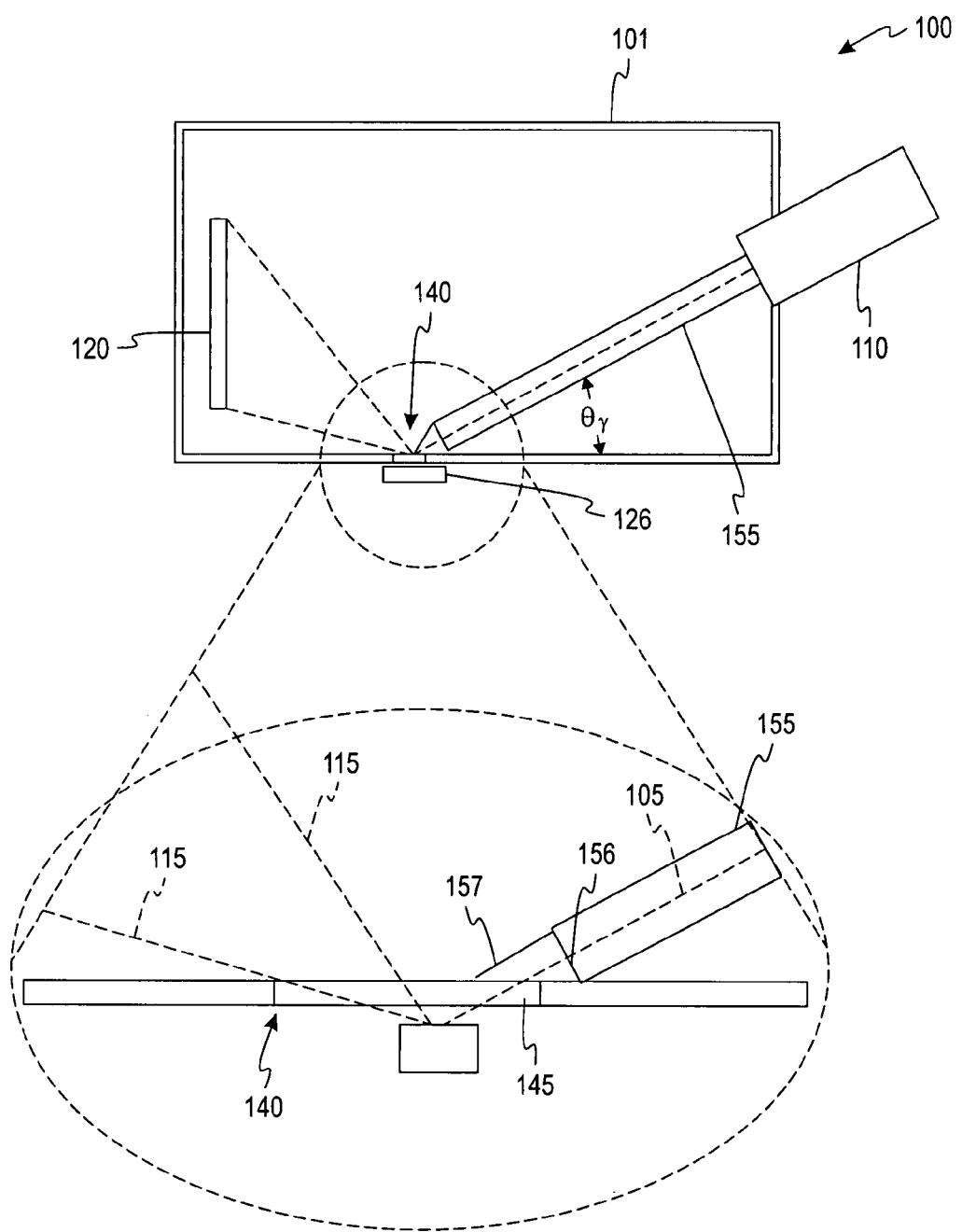

As shown in FIGS. 2a-2e, a sample 126 to be studied is positioned so that a collimated X-ray beam 105 emitted from the X-ray source 110 strikes the sample at a known position 125 ($x_o$,$y_o$,$z_o$) relative to the CCD(s) 120. The collimated X-ray beam 105 is, in the depicted geometry of FIGS. 2a-2e, in a plane generally bisecting the CCD 120 through the Y-axis and is parallel to the X-Z plane. However, the X-ray beam 105 need not bisect the CCD 120 through the Y-axis or be parallel to the X-Z plane to obtain useful data in accord with the present concepts. The known position 125 ($x_o$,$y_o$,$z_o$) is selected such that the CCD 120 captures a relatively large solid angle of rays emanating from the sample so that any arbitrary atomic plane separation (d-spacing) can be determined. As shown in the example of FIGS. 2a-2b, for example, the known position 125 ($x_o$,$y_o$,$z_o$) is located near one edge of the CCD(s) 120.

Although it is certainly preferred to provide a housing or enclosure 101, such as is shown in FIGS. 2b-2e, a housing is not required for all potential embodiments. The X-ray source 110 is fixed relative to the housing 101 and may be entirely disposed within the housing, partially within the housing, or external to the housing (e.g., with the emitted X-ray beam 105 passed through a window to an interior of the housing). It is preferred that the housing 101 is sealed (or sealable) to maintain a vacuum and correspondingly minimize any potential interactions between the X-ray beam 105 and a gas or gases therein. In some aspects, it may be desirable to include at least a minimal environment of certain gases, such as Helium. In still other embodiments, such as embodiments using higher energy X-ray sources or embodiments used in extraterrestrial applications, the housing environment may be open to the atmosphere or may maintain atmospheres not amenable to lower energy X-ray sources. The housing 101 is optionally shielded.

As shown in the examples of FIGS. 2a-2e, the housing 101 may optionally define a sample aperture 140 adjacent the known position 125 ($x_o$,$y_o$,$z_o$). The size and shape of the sample aperture 140, also represented in FIG. 2a, may be freely varied to accommodate the housing 101 configuration and to comport with an anticipated range of uses, desired data, and/or samples, such as shown by way of example in FIGS. 2c-2e. In various aspects of the present concepts, the sample aperture 140 comprises one (or more) fixed window(s) 145 and the known position 125 ($x_o$,$y_o$,$z_o$) is a position flush with, substantially flush with, or adjacent, an underside of the window(s) 145. The window(s) 145 may comprise any material, or combination of materials (e.g., layers), that is at least substantially X-ray transmissive along the Bremsstrahlung continuum (or a desired subset thereof). For example, the window(s) 145 may comprise a thin beryllium foil or disc, diamond, a polymer (e.g., Mylar™), boron nitride, or silicon nitride. In the example of a beryllium foil or disc, one current embodiment of window 145 is about 75 microns thick (about 0.003"). However, the thickness of the window and window material(s) for a given application vary in accord with variables known to those skilled in the art of X-ray diffraction and fluorescence to, for example, permit transmission of desired energies of X-rays without absorption.

Protective coatings and/or substrates (e.g., BR-127, aluminum, parylene N, DuraCoat™ by Moxtek, BerylCoat-D, gold, electroless nickel, etc.) may also advantageously be applied to the window(s) 145 in accord with anticipated environmental (e.g., temperature) and design considerations (e.g., X-ray energy level) for a given application.

In various aspects of the present concepts, such as are represented in FIGS. 2a-2e, for example, the housing 101 is sealed to form a vacuum environment therein or is selectively sealable to, in combination with a vacuum system, define a vacuum environment therein. In such aspects, the window (s) 145 serve(s) to separate the vacuum volume from the exterior environment to thereby maintain the vacuum environment while permitting X-rays to pass therethrough. However, in another aspect of the present concepts, the window(s) 145 may be omitted so that the sample aperture 140 provides an opening to the outside environment. In still another aspect, the window 145(s) may be configured as a movable shutter, manually or by a driving device, to selectively occlude the sample aperture during periods of use or non-use.

In other aspects of the present concepts, the optional sample aperture 140 may be omitted and, in lieu thereof, a sample load-lock door (not shown) provided in the housing 101 to permit samples to be introduced into and removed from the housing. In this configuration, the losses due to the use of an X-ray window 145 may be avoided. In aspects thereof, the housing may be evacuated, such as by using a vacuum pump to provide a vacuum of a desired quality.

The X-ray source 110 is optimized to produce a broad spectrum of X-ray wavelengths, such as by producing Bremsstrahlung continuum X-rays spanning between about the 0.1 keV to about the 10 keV band. In at least some aspects, the X-ray source 110 utilizes a 10 keV accelerating field with a high Z element electron impact source, such as gold, to produce Bremsstrahlung radiation with a few characteristic emission lines. In accord with other aspects of the present concepts, different targets and/or different accelerating potentials can be used to further optimize the spectral properties. In still other aspects, plural X-ray sources having the same or different characteristics may be disposed at different positions relative to the known sample position 125 (i.e., $x_0$, $y_0$, $z_0$). The X-rays are then collimated through a pinhole or optical system (e.g., a lens) to produce a small illuminated spot, typically about 1 mm in diameter, on the sample. For small samples, or where a precise location on the sample is to be examined, the sample may be mounted on an XYZ translation stage for positioning in at least some embodiments. Finally, because electron-impact X-ray sources 110 produce optical light, to which X-ray CCDs are sensitive, optical blocking filters, such as aluminized mylar, or baffling may be optionally used to prevent stray optical light from registering on the X-ray CCD 120.

Figure 2C:
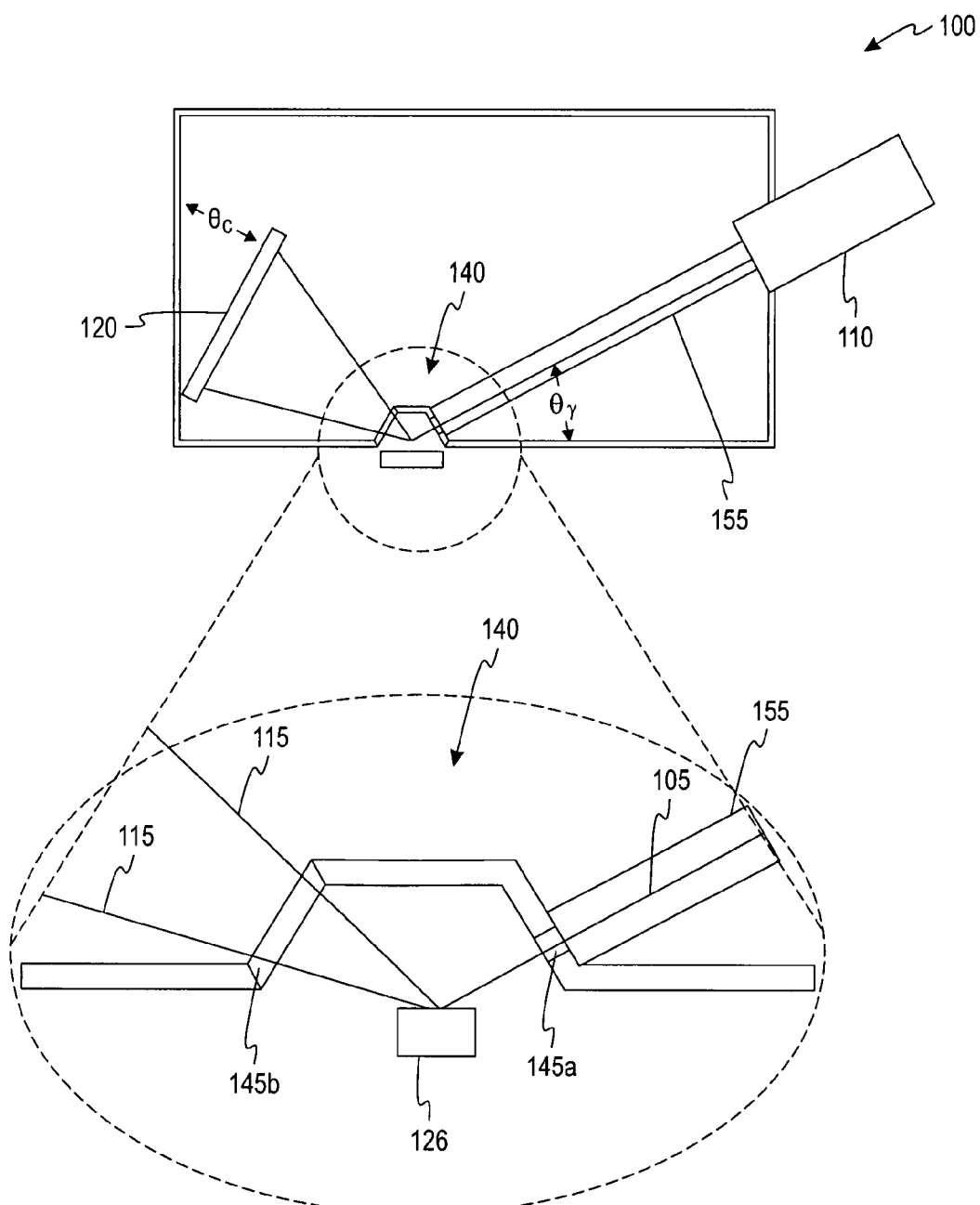
Figure 2D:
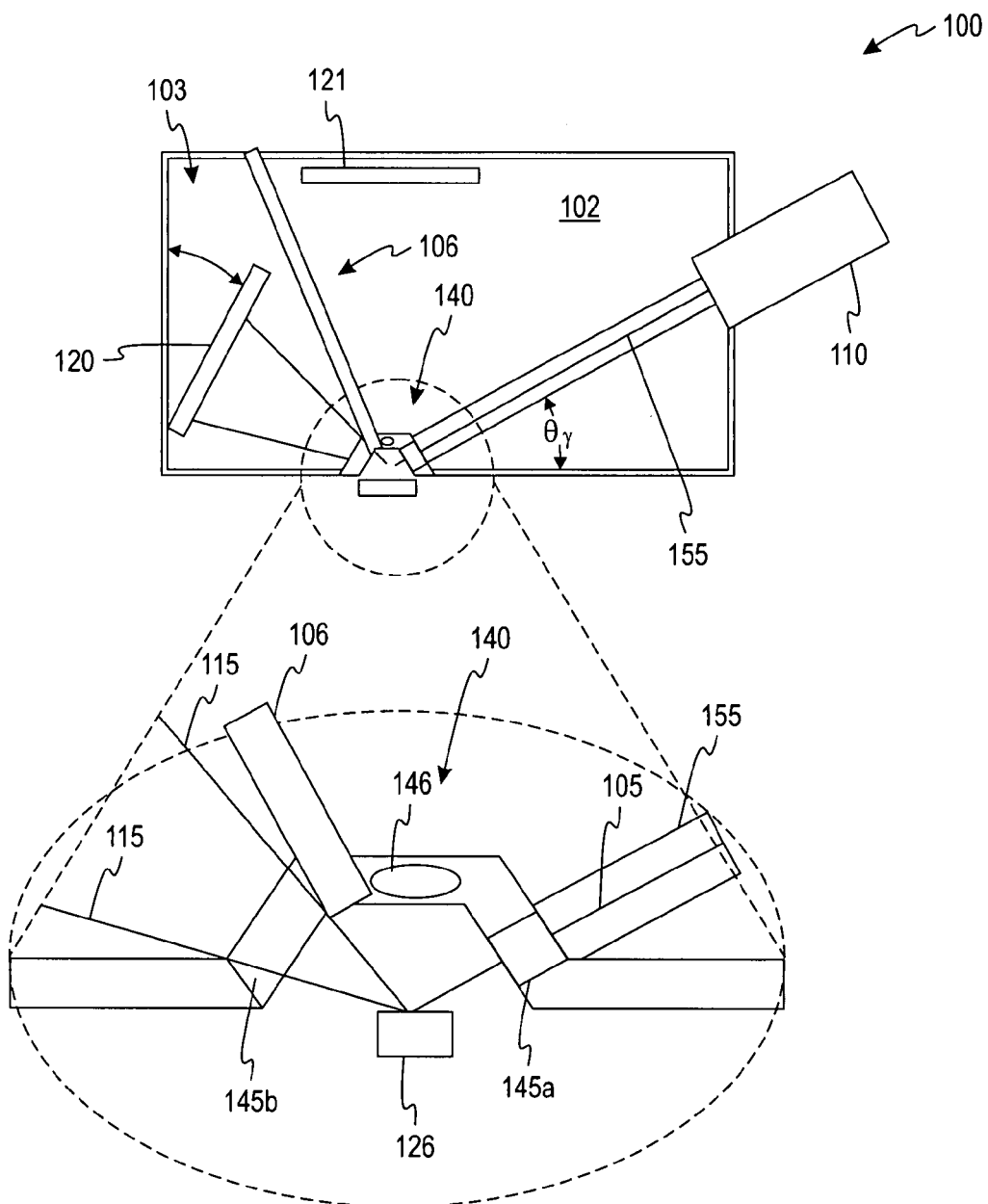
Figure 2E:
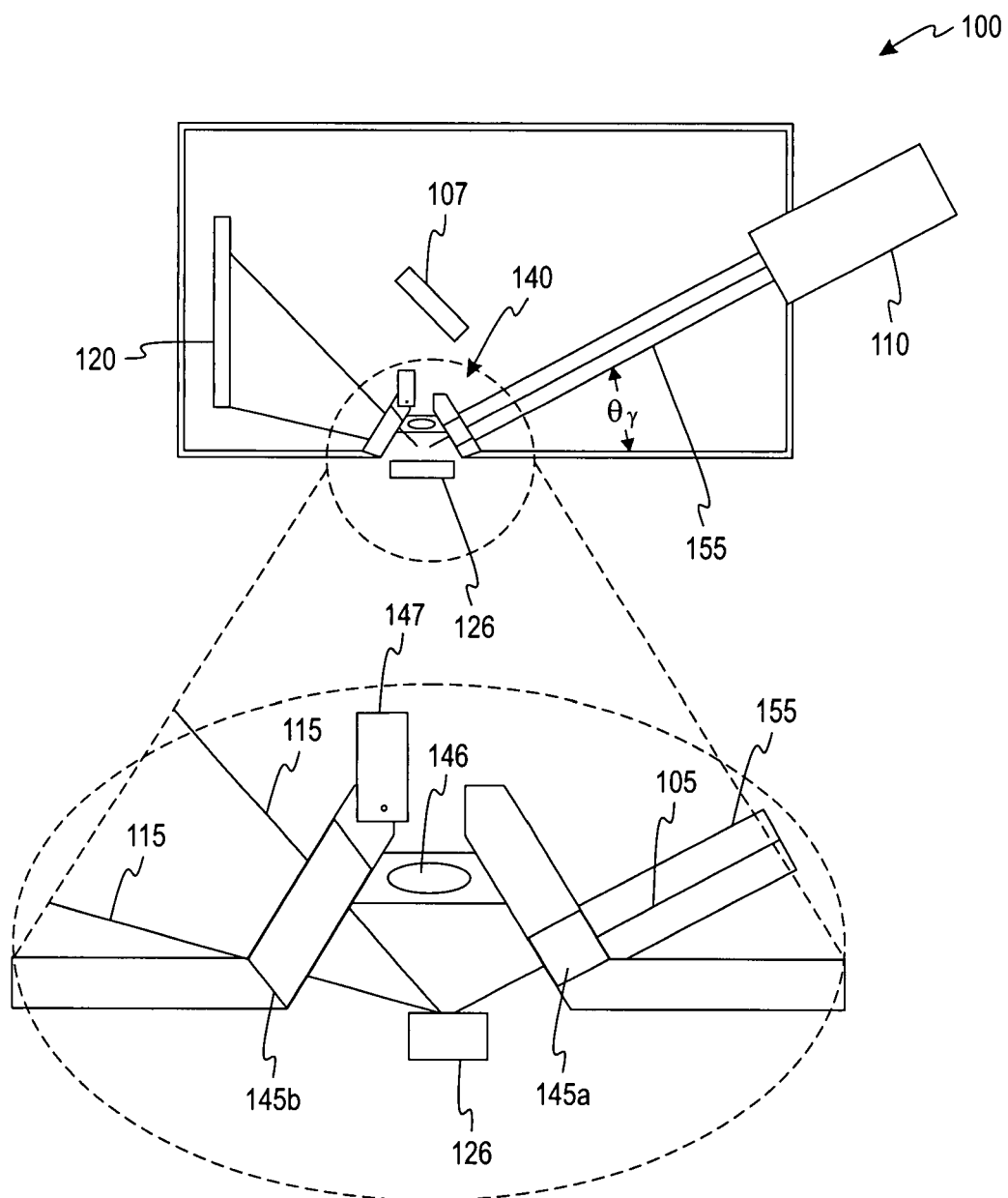

FIGS. 2a-2e show various embodiments of the sample aperture 140. FIG. 2a-2b show a sample aperture comprising a circular opening in which a window 145 is fixed. FIGS. 2c-2e show examples wherein the sample aperture 140 comprises a recessed portion in the housing 101, the recessed portion including a first window 145a and a second window 145b in peripheral portions thereof. The recessed sample aperture 140 geometry advantageously minimizes diffraction and fluorescence features from the Be window, achieving an effect similar to the shade 157 in FIG. 2b. The recessed sample aperture 140 geometry further increases design flexibility by increasing the available options for a fixed input angle for the X-ray beam 105 and a fixed output angle, or range of angles, for diffracted and fluoresced X-rays from the sample 126. Additionally, by providing two separate windows 145*a*, 145*b*, as opposed to a single window (e.g., 145 in FIG. 2*b*) the surface area of each of the individual window 145*a*, 145*b* is minimized relative to a single window configuration. This permits each of the windows 145*a*, 145*b* to be comparatively thinner than the single window 145, while retaining the same level of strength against the vacuum drawn in the housing in certain embodiments. FIG. 2*d* shows another variant of FIG. 2*c* comprising an optical lens 146 integrated into a bottom portion of sample aperture 140 (i.e., the "top" of the recessed portion, as shown). FIG. 2*e* shows a variant of FIG. 2*d* wherein a shutter is provided over the optical lens 146. The sample aperture 140 is not limited to the depicted configurations and may assume any configuration sufficient to permit X-rays (or other spectra of energy, such as optical light) from the X-ray source 110 to leave the housing 101 and to permit X-rays (or other spectra of energy) 115 output from a tested sample to enter the housing for registration on one or more appropriately configured energy detectors.

In the aspects shown in FIGS. 2*b*-2*e*, a collimator 155 is provided in the form of a brass tube having a proximal end disposed on or adjacent the X-ray source 110 and distal end disposed adjacent the window 145. A pinhole 156 is formed at the distal end of the collimator 155. Alternatively, other forms of collimator (e.g., lens(es), plates, shutters, etc.) may be used. In the embodiment of FIG. 2*b*, a shade 157 is also provided at the distal end of the collimator 155 to block X-rays diffracting and fluorescing from the window 145. In the embodiments of FIGS. 2*c*-2*e*, the distal end of the collimator 155 is disposed to abut, or at least substantially adjacent to, a first window 145*a* that is inclined relative to a bottom of the housing 101. In these aspects of FIGS. 2*c*-2*e*, a second window 145*b* is similarly inclined relative to a bottom of the housing 101. The second window 145*b* is configured to transmit the diffracted and fluoresced X-rays from the sample toward the CCD 120. As shown in FIGS. 2*c*-2*e*, the CCD 120 may be advantageously tilted toward the second window 145*b* by any desired angle $\theta_C$ (e.g., between about 0-45°, or greater angles, if desired). Likewise, the angle at which the first window 145*a* and second window 145*b* may be tilted may also assume any desired angle.

In FIG. 2*d*, the housing 101 is divided into a first vacuum chamber 102 and a second vacuum chamber 103 by a wall 106. An optical CCD 121 is disposed within the housing 101 in the first vacuum chamber 102 above the sample aperture 140 such that optical light transmitted through the optical (focusing) lens 146 from the sample 126 is incident upon the optical CCD. The wall 106 (i.e., a light-tight partition) serves to prevent stray optical light from introducing background noise on the X-ray CCD 120 and does not interfere with the diffracted and fluoresced X-rays leaving the sample 126 and going toward X-ray CCD 120. Thus, in the example of FIG. 2*d*, the XRD/XRF apparatus 100 provides for both X-ray imaging and optical imaging, simultaneously or separately.

FIG. 2*e* shows another variant wherein the wall 106 of FIG. 2*d* is omitted in favor of a mirrored surface 107 positioned to intercept and reflect incident optical light transmitted through optical lens 146 toward the X-ray CCD 120. In this configuration, the X-ray CCD 120 is utilized to perform optical imaging of the sample 126. A movable or actuatable shutter 147 is provided between the optical lens 146 and mirrored surface 107 and preferably adjacent the optical lens so as to selectively cover or expose the optical lens. The X-ray data and optical data could not be acquired at the same time in this configuration and the shutter 147 would be used to control optical exposures. In at least some aspects, the powering of the X-ray source 110 on and off could be used to control X-ray data acquisition.

The embodiments shown in FIGS. 2*d*-2*e* recognize that, in many applications, there is significant value in being able to examine visually a sample that is undergoing XRD and XRF analysis. For example, mineral identification is simplified considerably when optical characteristics such as color, reflectivity, and surface texture are available. Another advantage of optical imaging is that it allows for precise and reproducible positioning of samples. An illumination source, not shown in FIGS. 2*d*-2*e*, may be optionally provided to enhance optical imaging. In at least some aspects, the illumination source may comprise one or more white LEDs disposed adjacent the sample aperture 140 and/or adjacent the optical lens 146 to illuminate a sample. In another aspect, an illumination ring or rings (e.g., white light) may circumscribe a periphery of the optical lens and/or the sample aperture 140. Further or alternatively, one or more light sources having different characteristics (e.g., ultraviolet light (UV-A, UV-B, UV-C), infrared, etc.) may be utilized to provide enhanced analysis capabilities (e.g., fluorescence, phosphorescence, optically stimulated luminescence, triboluminescence, etc.).

The CCD 120 is coupled to CCD control and readout electronics 130, which in turn communicates, via a suitable hardwired or wireless communication path and/or communication interface, with a processor 135 configured to execute one or more instruction sets relating to event processing. From the X-ray capture event data output by the CCD 120, the processor 135 is able to generate a four-dimensional event list from the measured time, X-position, Y-position, and energy of each X-ray, data which will be described in greater detail below.

The CCD 120 comprises an array of pixels optimized for X-ray detection. In such a configuration, the CCD 120 can detect individual X-ray photons 115 and output to the processor 135, through the CCD control and readout electronics 130, information on the X-position and Y-position where the photons strike the CCD, as well as the energy (and thus the wavelength) of the individual X-ray photons. The CCD 120 continuously reads out images that are processed to extract the individual X-ray events containing position and energy information for each photon detected. As the CCD 120 information is received by the processor 135, individual photon events are identified and the event processing instruction sets, hardware, and/or firmware compiles a list or database of individual X-ray events. Each X-ray event is associated with a time (e.g., with resolution of the readout rate, typically seconds), position (e.g., X-position, Y-position), and energy (E). The processor 135 is operatively associated with at least one memory device (not shown) bearing the instruction set(s) controlling the event processing data operations and/or analyses and output devices for conveying information to a user. Execution of the sequences of instructions contained in the memory causes the processor 135 to perform the process steps described herein. Although the processor 135 is described in a singular form, the processor may comprise one or more processors in a multi-processing arrangement. The memory may comprise any computer-readable medium configured to store data and permit access thereto by a processor for execution including but not limited to, non-volatile media (e.g., optical or magnetic disks), volatile media (e.g., dynamic memory), and transmission media (e.g., signals received over coaxial cables, copper wire, fiber optics, or carrier waves, such as acoustic or light waves generated during radio frequency (RF) and infrared (IR) data communications). The processor 135 is also advantageously associated with a communication interface (e.g., ISDN card, modem, etc.) configured to provide data communication capability (e.g., transmission only or two-way coupling) to an external processor, computer, or network. In any such implementation, the communication interface would send and/or receive electrical, electromagnetic or optical signals that carry digital data streams representing various types of information.

In at least some aspects of the present concepts, the CCD 120 is a square or rectangular array having a width and height of several centimeters (e.g., 2.0, 2.5, 3.0, 3.25, 3.50, 3.75, 4.00, any values therebetween, etc.) with a pixel size of about 20-25 microns, or smaller. However, in still other aspects, the CCD 120 may comprise a larger CCD than the noted example (e.g., greater than 4.00 cm), a plurality of tiled or adjacently-disposed CCDs, and/or one or more non-planar CCDs. Thus, a plurality of CCDs 120 may be used to increase the area over which spectroscopic images are available, such as by disposing a plurality of CCDs (or other type of X-ray detector) around the known sample position 125 (i.e., $x_0$, $y_0$, $z_0$) and/or sample aperture 140, if provided, such as is shown by way of example in FIG. 3.

Figure 3:
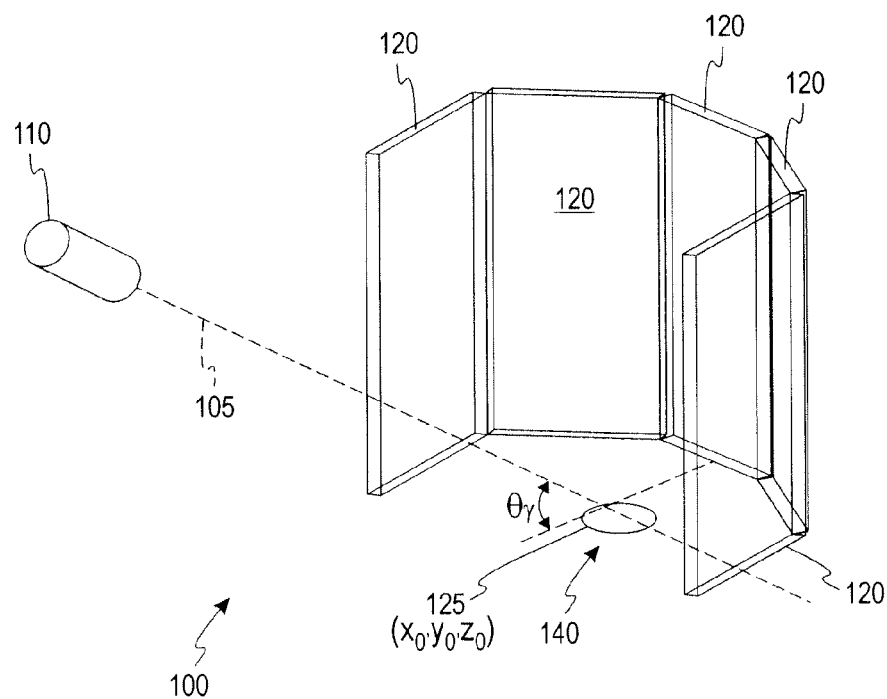
FIG. 3 shows a representation of aspects of another embodiment of an XRD/XRF instrument in accord with at least some aspects of the present concepts.

FIG. 3 shows a mosaic of CCDs 120 positioned to at least partially circumscribe the known sample position 125 (i.e., $x_0$, $y_0$, $z_0$) and sample aperture 140 to provide wide solid angle coverage. For example, the mosaic of CCDs 120 may span an arc of between about 180° up to and including 360°, or may span a lesser arc (e.g., 15°, 30°, 45°, 60°, 90°, 120°, or any smaller angle or intermediary angle, etc.). As shown in the example depicted in FIG. 3, the mosaic of CCDs 120 may span an arc slightly greater than about 180°. In still additional configurations, a plurality of CCDs 120 may be disposed to further provide X-ray detection capability along an upper portion of the XRD/XRF apparatus 100 (e.g., over known sample position 125 (i.e., $x_0$, $y_0$, $z_0$)). Such arrangements of CCDs may assume any geometry or shape, including for example, a hemispherical shape, a spherical frustum, or a polyhedral shape. Such multi-CCD 120 configurations provide a larger d-spacing range and/or finer d-spacing resolution, and increased sensitivity.

The CCD 120 is, at in some aspects of the present concepts, disposed in a housing 101 serving as a vacuum chamber. The CCD 120 is cooled to, for example, reduce thermally generated electrons in the detector and increase signal to noise ratio. However, cooling of the CCD 120 is not mandatory in all embodiments and it is expected that room temperature X-ray CCDs will be available in the near future.

The energy resolving power of the CCD 120 is energy dependent (e.g., the energy resolving power of the CCD 120 is typically about 2% at about 6 keV). The energy dependence of the energy resolution (full width at half-maximum, in eV) is given by:

$$\Delta E_{FWHM} = 2.354 \times 3.65 \times (N^2 + FE/3.65)^{1/2} \quad (1)$$

where N is the readnoise in electrons of the CCD and typically is 5 electrons, F is the "Fano Factor" for silicon and is typically about 0.1, and E is the photon energy in eV. X-ray CCDs differ from the usual CCD in that their detection volume (the "depletion" region) is thicker so as to make it more sensitive to more penetrating radiation. To achieve the deep depletion the base material of the X-ray CCD is of a higher purity and thus higher-resistivity silicon than in normal optical CCDs. As discussed below (see, e.g., FIG. 16), the single-photon energy measurement capability of the CCD 120, or other X-ray detector, is the dominant term in the "error budget" that determines the d-spacing measurement resolution of a continuum spectrum of X-rays based diffraction instrument.

Referring back to FIGS. 2a-2b, for example, X-rays coming from the sample produced by fluorescence (XRF) are emitted with no specific directionality and will be captured by the CCD 120 with no spatial patterning, apart from $1/r^2$ and solid angle projection effects. The XRF X-rays, however, carry information about the elemental make-up of the sample through the characteristic X-ray lines they emit. In this regard, it is noted that the reflection geometry provided by the XRD/XRF apparatus 100 provides less self absorption in the sample than is possible in a transmission geometry, allowing for the measurement of lower energies and for the performing of a better and more quantitative calibration procedure. Still further, for a given d-spacing range and resolution, the XRD/XRF apparatus 100 can use a X-ray beam 105 having comparatively larger spot sizes (e.g., about 1 mm in diameter rather than about 0.05 mm in diameter) to provide a larger XRF signal for the same X-ray source 110 power. Use of a continuum spectrum of X-rays to excite XRF in the sample up to the cutoff energy of the X-ray source 110, as opposed to using a characteristic line to excite XRF in the sample up to a much lower energy, allows the XRD/XRF apparatus 100 to more efficiently and completely excite XRF than conventional XRD/XRF apparatus 10 and techniques. For example, for conventional XRD/XRF apparatus 10 using Co Kα X-rays from the source, which is less efficient at exciting XRF from, for example, Sulfur than continuum photons (as utilized in the XRD/XRF apparatus 100 disclosed herein) just above the S-K edge while such Co Kα X-rays are incapable of exciting XRF from higher Z elements, such as Fe or Ni.

Diffracted X-rays, in contrast, emerge from the sample in specific directions consistent with Bragg's law:

$$n\lambda = 2d \, \text{SIN}(\theta) \quad (2)$$

where λ is the wavelength of the X-ray photon, d is the atomic plane spacing for the tested material, 2θ is the diffracted angle, and n is the diffraction order. The diffraction angle θ is coded in the X-Y plane of the CCD 120. In FIG. 2a, the dashed arc 122 in the CCD 120 X-Y plane represents, for example, where a diffracted angle of 2θ would intersect the CCD. Generally, as the CCD 120 X-position increases, so does the diffraction angle.

When the collimated X-ray beam 105 strikes the sample, some of the X-rays forming the X-ray beam are diffracted in accordance with Bragg's Law. The strongest X-ray diffraction occurs when the angle of X-ray incidence on an individual series of atomic planes equals the angle of exit (i.e., specular reflection). Some of the X-rays are stopped in the sample where the energy deposited thereby causes individual atoms to produce characteristic X-ray emission lines with known wavelengths through X-ray fluorescence (XRF). Whereas monochromatic X-rays striking a sample containing crystallites of a given atomic-plane spacing d and oriented in slightly different directions may result in constructive interference from just one of the crystallites, as determined by Bragg's law, providing a range of wavelengths in accord with the present concepts permits accommodation of a range of crystallite orientations and extends the instrument's ability to probe the crystal structure of the sample. The CCD 120 captures a large solid angle of both diffracted and fluoresced X-rays and outputs the event information to the processor, as noted above, where the processor assimilates the event information and produces an event list describing the interaction points (x, y, z), wavelength (λ), time and/or energy (E) of each individual X-ray photon detected by the CCD 120. The event list may comprise any subset of the aforementioned data (e.g., only x-position, wavelength, and energy, etc.) and is not required to include all of the above data points.

The event list data can be filtered to examine particular subsets of information including, for example, plotting only those photons consistent with diffraction from a single d-spacing to thereby directly image the size and orientation distributions for crystal grains containing that d-spacing. Furthermore, because photon detections are optionally time-tagged (with the intrinsic resolution of the X-ray detector), time-dependent material analysis is also possible in accord with at least some aspects of the present concepts. Time-tagging, together with the high sensitivity of the XRD/XRF instrument 100, allows for measurements of phenomena that evolve with time such as, but not limited to, changing crystal structure (e.g., d-spacings, degree or quality of crystallization in growth and degradation, grain sizes and shapes, crystal texture, etc.) or changing chemical makeup (e.g., monitoring elemental abundances through XRF during a chemical reaction, etc.). Further, as to crystal texture analysis, the methods described herein fully exploit the XRD/XRF instrument 100 data to compute d-spacings for individual photons, filtering event lists for successive d-spacing values and plotting the resulting detector images, optionally in polar coordinates to eliminate distortion. Photons are presently tagged with a readout time with a resolution of a few-seconds resolution. However, faster CCD 120 readout electronics and/or utilization of a pulsed or modulated X-ray source 110 can improve this time resolution.

Figure 4:
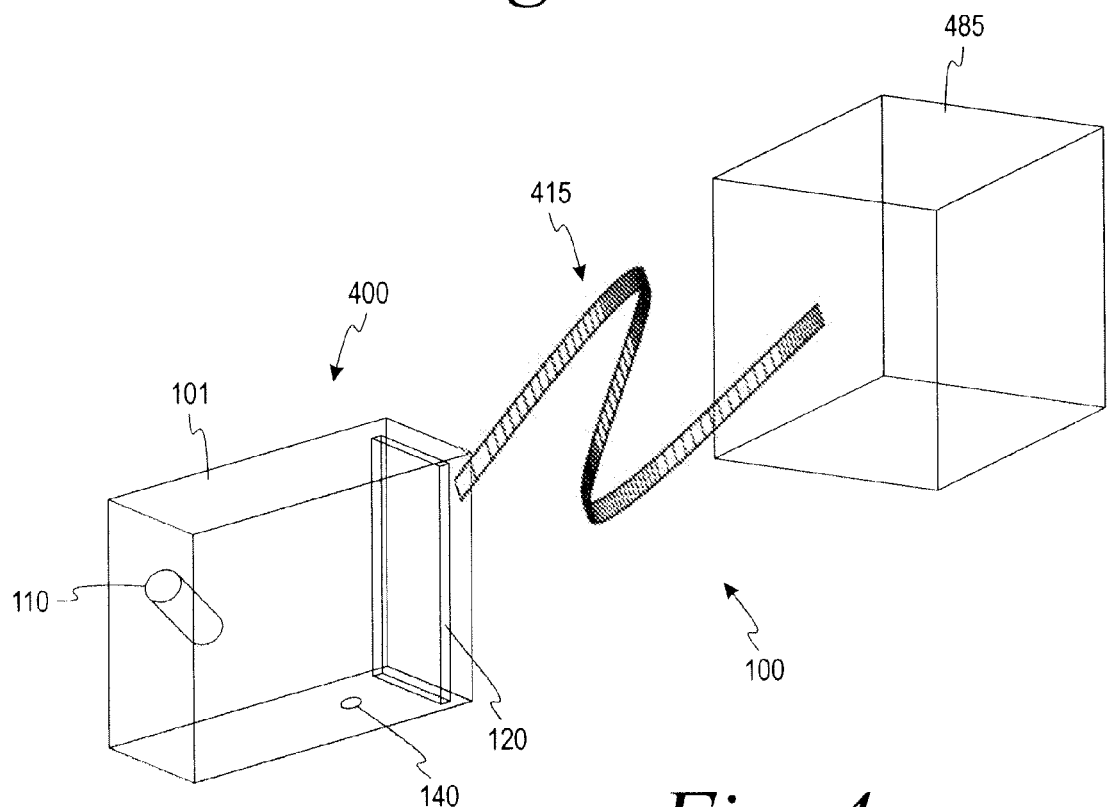
FIG. 4 shows a representation of one implementation of an XRD/XRF instrument in accord with at least some aspects of the present concepts.

FIG. 4 shows one embodiment of at least some aspects of a XRD/XRF instrument 100 in accord with the present concepts. The XRD/XRF instrument 100, comprising the broad spectrum collimated X-ray source 110 and the CCD 120 are disposed in a small sensor head 400. The sensor head 400 is connected to a control system 485 via a cable 415. The local control system 485 comprises, for example, CCD control and readout electronics, processor(s), memory, power supply, and associated software, firmware, and/or hardware necessary to perform event processing for the CCD 120 event data.

The sensor head 400 may be made to be less than about 5 centimeters on a side and is mountable, if desired, on a robotic arm (not shown), such as may be provided on an extraterrestrial landing vehicle, law enforcement robotic vehicle, or the like. The sensor head 400 may optionally comprise shielding to eliminate any X-rays not originating from X-ray source 110. In operation, the sensor head 400 would be placed on top of a sample so that a portion of the sample disposed at the known sampling position 125 ($x_o$, $y_o$, $z_o$) could be illuminated by the X-ray beam (not shown). One or more sensors such as, but not limited to, a touch sensor, laser range finder, or mechanical rest may be advantageously utilized to ensure the sample is appropriately positioned. The data would then be output via a cable 415, or via some other suitable wired or wireless communication path, to an associated processor 135, whether disposed in the local control system 485 or remotely disposed.

In at least some aspects, the software, firmware, and/or hardware (e.g., electronics) required to control the operation of the sensor head 400 (e.g., CCD controller, event extractor, computer interface, event logger, and/or other software, firmware, and/or hardware) may be integrated within or on the sensor head and/or may be disposed remotely, in whole or in part, in the robotic vehicle or other platform external to the sensor head. Electrical communication between the sensor head 400 and any remote software, firmware, and/or hardware may be achieved by use of a flexible signal cable (e.g., a cable routed through or on a robotic arm) and/or wireless communication device(s) (e.g., using Bluetooth or other wireless communication protocol). Power may be provided to the sensor head 400 the robotic vehicle or other platform through cable 415 or through a dedicated power cable, preferably routed directly through or on the robotic arm (not shown).

In any portable unit, such as sensor head 400, the CCD 120 and X-ray source 110 vacuum volumes (e.g., vacuum chamber of housing 101 or separate vacuum chambers) would have to be maintained without large mechanical, cryogenic, or diffusion pumps. In these instances, techniques similar to those used for commercial sealed electronic X-ray tubes (e.g., heat- or chemically-activated gas getters) may be employed. Welded joints and/or metal gaskets may be used in lieu of rubber or viton to minimize permeability of the sensor head 400. These approaches may facilitate further miniaturization of embodiments of the disclosed XRD/XRF instrument 100 deployed in a sensor head 400.

It is to be understood that the present concepts are not limited to any particular size, arrangement, or geometry of CCD(s) 120, subject to the above-noted requirement to sufficiently resolve the position and energy of individual X-ray photons and output to a processor information relating thereto. In at least one embodiment, the CCD 120 may comprise the Event Driven CCD (EDCCD), Gen 1.0 device, or successor devices, fabricated at the Massachusetts Institute of Technology (MIT) Lincoln Laboratory. The apparatus and methods disclosed herein are not limited to a CCD 120 X-ray detector or detectors and, in various aspects, may utilize a X-ray detector other than a CCD 120, such as another type of solid-state imaging X-ray detector (e.g., active pixel silicon detectors), single-photon spectroscopic area detector, combinations of CCDs with other detectors (e.g., CCD to cover low energy part of XRD/XRF work with CZT array to cover diffraction or scattering of higher energy X-rays or large, cheap imaging proportional counters in combination with strategically located CCDs), Tunnel Junction detector arrays, X-ray microcalorimeter arrays, and/or imaging proportional counter. As noted above, the energy resolution of the selected energy-resolving imaging photon-counting detector will drive the performance of the XRD/XRF instrument 100 in regards to d-spacing resolution (see, e.g., FIG. 16).

Figure 5A:
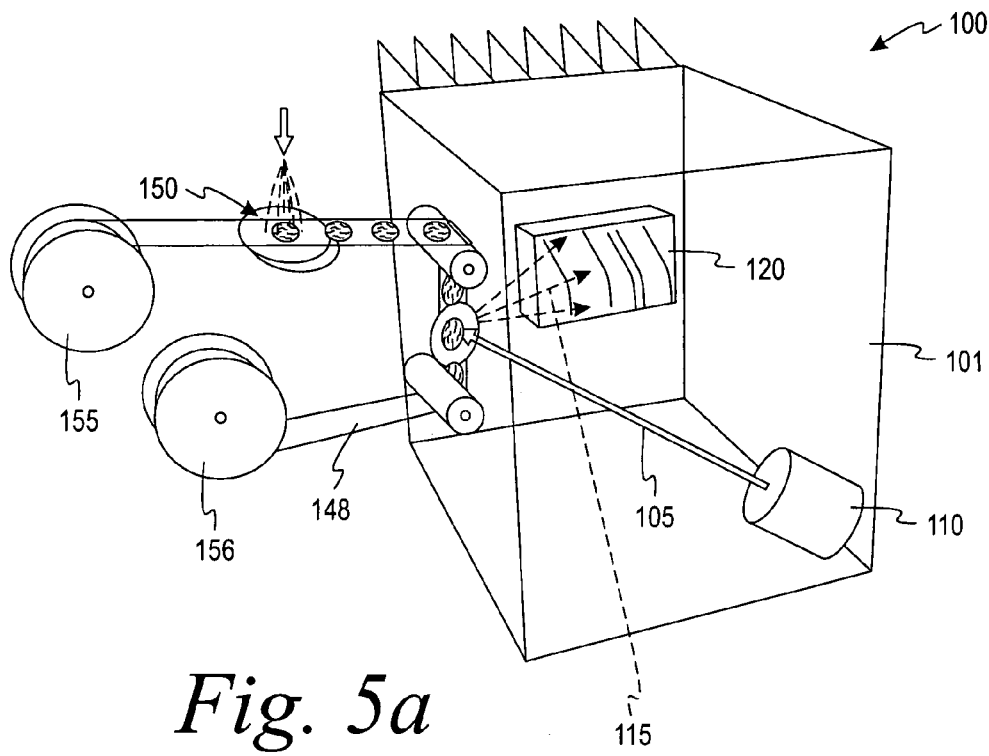
FIGS. 5a-5b depict embodiments of XRD/XRF instruments in accord with still additional aspects of the present concepts.

FIG. 5a shows one embodiment of at least some aspects of the present concepts wherein the XRD/XRF instrument 100 is configured to provide real-time aerosol collection and analysis. As with the previous examples, the X-ray source 110 is configured in a reflection geometry to output an X-ray beam 105 to a known position ($x_0$, $y_0$, $z_0$) (not shown) from which point X-rays 115 are diffracted toward CCD 120. However, it is to be noted that these concepts are not limited to real-time aerosol collection and analysis in a reflection geometry and the concepts described herein apply equally to aerosol analysis of a prepared or unprepared sample in transmission geometry (e.g., using a thin collecting tape, using a disk system and rotating the disk like a filter wheel with discrete positions or even continuously in front of the X-ray beam, etc.). In the depicted example of FIG. 5a, particles are collected on a tape 148 aerosol collection substrate 150 by impactation, filtration, or electrostatic precipitation (e.g., needle to plate electrostatic precipitator), and then the substrate 150 is moved (e.g., automatically) by a drive system to the sample aperture 140 for analysis. The tape 148 may comprise, but is not limited to, a polycarbonate or other synthetic material. In at least some aspects, the collecting tape may comprise a first roll 155 of tape bearing a supply of clean aerosol collection substrate and a second, take-up roll 156. In another alternative embodiment, the reels 155, 156 may be omitted and an aerosol collection substrate holder, port, or ported vacuum chamber may be provided to hold an aerosol collection substrate 150 (e.g., manually or automatically inserted) during analysis. Optical probes (not shown) may optionally be provided externally to the XRD/XRF instrument 100 to provide complementary information on size, refractive indices, etc.

Figure 5B:
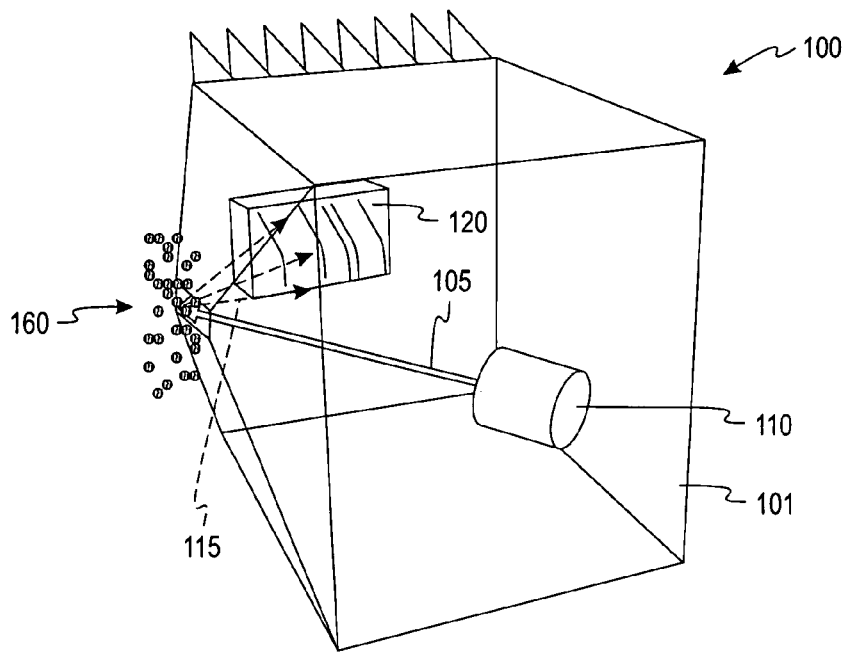

FIG. 5*b* shows yet another embodiment of at least some aspects of the present concepts wherein the XRD/XRF instrument 100 is configured to provide a real-time "flyby" particle measurement system. As with FIG. 5*a*, the X-ray source 110 is configured in a reflection geometry to output an X-ray beam 105 to a known position ($x_0$, $y_0$, $z_0$) (not shown) from which point X-rays are diffracted toward CCD 120. In this example, particles 160 are not collected on an aerosol collection substrate, but are rather measured while suspended in the atmosphere. Particles may include, for example, but are not limited to, aerosols or ice.

Figure 6:
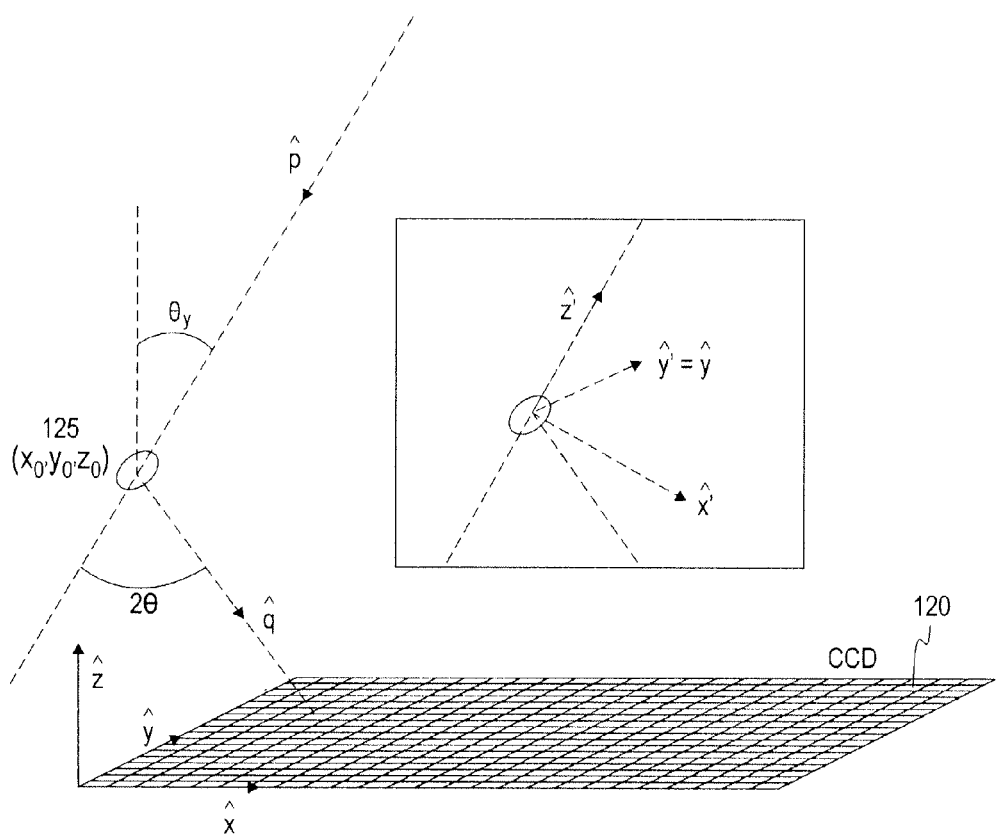
FIG. 6 depicts a relation between a sample and an origin of a CCD and an X-ray source vector in accord with at least some aspects of the present concepts.

FIG. 6 shows an illuminated spot of a sample material and highlights the deriving of the quantity 2θ for an arbitrary position on the CCD 120.

A coordinate system is established with an origin at a pixel (row 0, column 0) of the CCD 120, with the CCD shown to lie in the (x,y) plane. Unit vectors are shown. The incoming photon direction is defined by the vector $\hat{p}$ (i.e., the X-ray source vector) and the diffracted beam is defined by the vector $\hat{q}$, with the illuminated spot on the sample at position ($x_0,y_0,z_0$). For the following illustrative remarks, it is assumed that $\hat{p}$ lies in the (x,z) plane.

The incoming and outgoing photon vectors may be defined as follows:

$$\hat{p} = -\sin\theta_\gamma \hat{x} - \cos\theta_\gamma \hat{z} \quad (3)$$

$$\hat{q} = \frac{\vec{q}}{|\vec{q}|} = \frac{(x-x_0)\hat{x} + (y-y_0)\hat{y} - z_0\hat{z}}{\sqrt{(x-x_0)^2 + (y-y_0)^2 + z_0^2}}. \quad (4)$$

Then:

$$\cos(2\theta) = \hat{p}\cdot\hat{q} = \frac{-\sin\theta_\gamma(x-x_0) + \cos\theta_\gamma z_0}{\sqrt{(x-x_0)^2 + (y-y_0)^2 + z_0^2}}. \quad (5)$$

Bragg's law links d to sin(θ), so the following trigonometric identity is useful:

$$\cos(2\theta) = 1 - \sin^2\theta. \quad (6)$$

It is possible, then, to compute d as a function of photon position and energy, without any trigonometric computations:

$$d = \frac{n\lambda}{\sqrt{2 - 2\cos(2\theta)}}, \quad (7)$$

where cos(2θ) is given above (note that sin θ$_\gamma$ and cos θ$_\gamma$ are constants for a fixed geometry). To derive azimuthal angle, φ, around a diffraction cone intercepted by a flat surface, the origin is first translated (in all three dimensions) to the illuminated spot on the sample, so that an arbitrary point ($x_d$, $y_d$) on the detector has coordinates $$(x,y,z) = (x_d - x_0, y_d - y_0, -z_0) \quad (8)$$

The coordinate system is then rotated by −θ$_\gamma$ (i.e., clockwise) about ŷ, so that the z' axis is anti-parallel to the incoming photon direction. The pixel coordinates under this rotation transform to:

$$x' = x\cos\theta_\gamma - z\sin\theta_\gamma$$

$$y' = y$$

$$z' = x\sin\theta_\gamma + z\cos\theta_\gamma. \quad (9)$$

Because the vertical axis is now aligned with the axis of the diffraction cone, the azimuthal angle around the cone is just $$\phi = \tan^{-1}\left(\frac{y'}{x'}\right) \quad (10)$$
$$= \tan^{-1}\left[\frac{y_d - y_0}{(x_d - x_0)\cos\theta_\gamma + z_0\sin\theta_\gamma}\right].$$

The intersection of a cone and a plane traces out a circle, ellipse, parabola, or hyperbola depending on the relative orientations of the cone's symmetry axis, its "generator" lines, and the plane's normal vector. The only case in which diffraction arcs on a CCD will be circular is in the transmission configuration where θ$_\gamma$=0. In reflective geometries, such as relates to the disclosed examples of FIGS. 2*a*-2*e*, 3, 4, and 5*a*-*b*, for θ$_\gamma$>0, the diffracted X-rays form arcs on the CCD 120, or other detector, that are parts of ellipses, a parabola, and hyperbolae, all at the same time, depending on the value of θ$_\gamma$ relative to 2θ. The arc will be part of an ellipse if 2θ<(π−θ$_\gamma$), part of a parabola if 2θ=(π−θ$_\gamma$), and a hyperbola if 2θ>(π−θ$_\gamma$).

The derivations above assume that CCD positions (x,y) are known and the polar angles (θ,φ) must be solved for, as is appropriate for analyzing data. In a simulation, however, we will typically want to specify the crystal(lite) orientations (θ,φ) and solve for the detector coordinates of diffracted photons. To simulate a powder sample, for example, the azimuthal angle φ would be drawn from a uniform distribution, while the mineral d-spacing and photon wavelength determine θ through Bragg's law.

Using the following definitions, C≡cos(θ$_\gamma$), S≡sin(θ$_\gamma$), Z≡$z_0$, P≡tan(φ), and T≡cos(2θ), the equations for cos(2θ) and tan(φ) above can be merged and the quadratic solved for X≡x−$x_0$ and Y≡y−$y_0$:

$$X = \frac{-b + \sqrt{b^2 - 4ac}}{2a} \quad (12)$$
$$Y = P[XC + ZS]$$

wherein the second root for X is only of interest in transmission geometries, and where $$a = T^2(1 + P^2C^2) - S^2$$

$$b = 2SCZ(1 + T^2P^2).$$

$$c = Z^2(T^2 + T^2P^2S^2 - C^2) \quad (13)$$

The placement of the sample (e.g., sample 126 in FIG. 2*b*), at the known position 125 ($x_o,y_o,z_o$) may be advantageously facilitated by one or more sensors (not shown) disposed in or adjacent the known position ($x_o,y_o,z_o$), sample aperture 140, and/or window 145. Such sensor(s) may include, but are not limited to, physical devices (e.g., pressure sensor, force sensor(s), resistive touch screen panel/overlay, surface acoustic wave touch screen panel/overlay, guided wave touch screen panel/overlay, infra-red touch screen panel/overlay, contact switch(es), proximity switch(es), etc.) or optical devices (e.g., laser(s), camera, devices, etc.). To the extent that a sample may not be precisely positioned at the known position 125 ($x_o$, $y_o$, $z_o$), the positional data output by the sensor(s) may be advantageously utilized by the processor to introduce corrections or transformations, as needed, for the data obtained from CCD 120.

To compute diffraction angles from detector coordinates, the collimated X-ray beam 105 direction and the position of the illuminated spot on the sample 126, relative to the detector 120 origin, must be known. Although the X-ray beam 105 direction and location are constant for a given XRD/XRF instrument 100, the placement of the sample 126 and irregularities in its shape can alter the precise location of the illuminated spot. In practice, incoming rays may be slightly converging or diverging, while the illuminated spot will have some non-zero extent, usually in x and z. These complications can degrade the d-spacing measurement resolution, but their effects are easily modeled and limited. In the simple configuration of FIG. 2a, the geometry is fully characterized by three parameters: $x_0$, $z_0$, and $\theta_\gamma$, with $y_0$ fixed by construction (e.g., along the centerline of the CCD 120 in FIG. 2c). The values of these parameters can be derived, if no other means exists to measure them directly (e.g., optical imaging), by obtaining data from a calibrator sample, any substance that exhibits at least three d-spacings within the XRD/XRF instrument's 100 range. Aluminum serves very well (see FIGS. 7a-7e) for this purpose. Because two of the three parameters (the slope $\theta_\gamma$ and an intercept) describe the fixed X-ray beam 105 line, they apply equally to all other datasets acquired with the same XRD/XRF instrument 100, leaving only a single parameter (i.e., position along the beam line) to be solved for subsequent samples. This can be accomplished by, among other means, cumulating d-spacing histograms over a range of possible sample positions and choosing that which produces the highest signal-to-noise ratio peaks.

The CCD 120 accumulates photons for a fixed exposure time (e.g. 10 seconds or less), putting out a sequence of images which are then processed to extract the individual X-ray events containing position and energy information. CCD 120 readout electronics produce an amplified signal proportional to the charge produced in each pixel by ionizing X-ray photons. To perform single-photon spectroscopy, this pixel charge information must be scanned and analyzed for local excesses, possibly distributed over multiple pixels. Techniques to accomplish this have been refined and are well known in the field of X-ray astrophysics. For field units, these algorithms may be implemented on field programmable gate array (FPGA) electronics for portability and speed of execution. As the CCD 120 is read out and individual photon events are identified, a list of single-photon properties is compiled by the processor 135 in an event list comprising time (with resolution of the readout rate), position, and energy.

The CCD 120 is reporting $\theta$ and $\phi$ (the azimuthal angle along diffraction cones) encoded in X and Y, as well as energy for all events. The energy (E) measured by the CCD 120 may be converted into a wavelength $\lambda$ using the quantum physical relation:

$$\lambda = hc/E \quad (14)$$

where h and c are Planck's constant and the speed of light, respectively, and the product hc=12400 eV-Å. The X-ray source is producing a broad bandpass of $\lambda$s. By plotting E vs. $\theta$ for all the X-ray events in the event list, it can be seen how the diffracted X-rays differentiate themselves from XRF X-rays. Specifically, related XRF information appears as a constant in the E vs. $\theta$ space, while related diffracted X-ray photons would follow (reciprocal) SIN functions with amplitude proportional to twice the atomic plane spacing (d) of the material in the sample. Thus the XRD/XRF instrument 100 is simultaneously providing elemental composition from the XRF data as well as more specific atomic plane spacing (d) information from the XRD data. Combined, this information can then be used to identify the sample.

If Bragg's Law (Eq. 2) is applied to the geometry described above, data from each event may be used to convert x and y to diffraction angle $\theta$ and cone azimuth $\phi$, convert event energy to wavelength $\lambda$, and calculate the expected d-spacing if that event was due to XRD. From this information, the data may be plotted in the space of energy vs. d-spacing, where XRF and XRD features of interest are orthogonal (e.g., FIG. 7b, discussed below). In these diagrams, the "banana" envelope of the photon events reflects the boundaries of the CCD detector in 2$\theta$, consistent with Bragg's law. For the Al 6061 sample data in FIGS. 7a-7e, this envelope corresponds to 38° along the upper boundary, and 72° along the lower boundary. To form crude energy and diffraction spectra, this two-dimensional information can be collapsed horizontally and vertically. For quantitative analysis of a diffraction spectrum ("diffractogram"), however, it is important to account for the different energy bandwidths/bandpasses and detector areas that are cumulated into the various diffractogram bins. This normalization changes the relative ratios of the amplitudes of diffractogram peaks, which carry information about mineral phase, mineral abundances, and crystal texture. Both normalized and unnormalized diffraction spectra are plotted in some of the sample data discussed below. Mixed XRD/XRF data may be analyzed, in accord with at least some aspects of the present concepts, through energy filtering, 2-D Fourier filtering (E vs. 2$\theta$ or E vs. d), and/or 2-D simultaneous matched filtering. Diffractograms are normalized per energy bandwidth and detector area.

The XRD/XRF instrument 100 described herein captures additional information as well due to specular reflection (i.e., perfect reflection in which an X-ray from a single incoming direction ($\theta i$) relative to a surface normal is reflected into a single outgoing direction ($\theta r$) relative to the surface normal wherein $\theta i$ is equal to $\theta r$). If, for example, the sample 126 disposed at the known sample position 125 in FIG. 2b were a perfect crystal with atomic planes disposed parallel to the Y-Z plane, then the brightest X-ray diffraction peak would occur at an angle equal to the incident angle of the collimated beam 105 on the sample. This would happen at a particular wavelength ($\lambda$) consistent with Bragg's Law (Eq. 2). Since the X-ray source 110 produces a broad range of wavelengths $\lambda$, this condition will be satisfied. Further, the CCD 120 X-Y image defines an image of the X-ray source 110 with a size comparable to the footprint of the collimated X-ray beam 105 on the crystal. If the crystal in this example were to be tipped toward the CCD (i.e., rotated about the Y-axis) then the image would move along the X direction of the CCD (and the wavelength would change). If the crystal were rotated about the Z-axis, then the image would shift azimuthally along an arc of constant 2$\theta$. If the crystal were smaller than the footprint of the collimated X-ray beam striking the crystal, then the size and shape of the reflected image would correspond to the crystal's size and shape. If the sample is composed of many small crystal or domain facets, then the image would describe the granularity and crystalline texture of the sample by providing size and orientation (i.e., tip-tilt of crystal grains) distribution information.

The use of Bremsstrahlung continuum X-rays, or a "white light" approach, to XRD and XRF in accord with the present concepts provides many important advantages over traditional monochromatic techniques. At the same time, this broad spectrum approach presented a data-reduction challenge regarding the simultaneous analysis of XRD and XRF features in the same broadband data stream. In accord with the present concepts, the diffraction and fluorescence properties of a sample can be isolated and characterized with varying levels of sophistication, such as by alternately masking out horizontal or vertical features in energy vs. d diagrams (e.g., FIG. 7b or FIG. 8), by applying a Fourier filter to the image, or by simultaneously fitting all observed features to a model of the instrument and the sought-after properties of the sample. Other forms of analysis, whether conventional analysis tools in X-ray astrophysics or analysis tools yet to be developed are all utilizable in accord with the present concepts. The first approach noted above, masking, is trivial to implement and provides gross separation of the XRF and XRD information. The second approach, two-dimensional Fourier filtering, neatly distinguishes, in most cases, the horizontal and vertical features, allowing for standard fluorescence and diffraction (e.g., Rietveld) analyses on the resulting one-dimensional spectra. The third approach, simultaneous fitting, involves applying an accurate model of the instrument's response to a variety of assumed source properties and fitting for the best match. A high-fidelity model of the instrument allows for well-calibrated datasets, while simultaneous fitting for fluorescence and diffraction increases sensitivity to weak features.

A first and a second prototype XRD/XRF instrument 100 in accord with the present concepts were built and respectively correspond to FIGS. 2a and 2b. A third prototype XRD/XRF instrument 100 is being built to correspond to the arrangement depicted in FIG. 2c. The first and second prototypes comprise(d) a 10 keV electron impact X-ray source (Austin Instruments, Model 2—Mason Source) and a commercially available X-ray CCD 120 with 20 micron pixels (Princeton Instruments Model 7509-0007 and Princeton Instruments Model 7510-0006, respectively). Data samples described below are from the second prototype (see FIG. 2b), which comprises a 1340×1340-pixel CCD 120 (26.8 mm×26.8 mm active area). The X-ray source 110 comprises a gold-plated (Au) copper (Cu) target to produce strong Bremsstrahlung continuum, as well as Au M characteristic lines (e.g., $M_{\alpha 1}$, $M_{\alpha 2}$, $M_\beta$, $M_\gamma$). Referring to the configuration depicted by way of example in FIGS. 2a-2b, the first prototype XRD/XRF instrument 100 was configured with $\theta_\gamma$=28.5° relative to the Y-Z plane and $x_o$=−1.9 mm, $y_o$=4.0 mm, and $z_o$=33 mm relative to the lower right corner of the CCD 120. The second prototype XRD/XRF instrument 100 was configured with $\theta_\gamma$=30.0 degrees and a known sample position 125 at coordinates of $x_o$=−3.9 mm, $y_o$=13.4 mm, and $z_o$=34.7 mm, all measured relative to the lower right corner of the CCD 120. The third prototype XRD/XRF instrument 100 was configured with $\theta_\gamma$=30.0 degrees and a known sample position 125 at coordinates of $x_o$=4 mm, $y_o$=13.4 mm, and $z_o$=25 mm, all measured relative to the lower right corner of the CCD 120. The beam current was variable between 50 and 300 micro-Amps. For the following examples, no sample preparation was performed. The samples were merely disposed at the known sample position 125 ($x_o$,$y_o$,$z_o$). The X-ray spot size on the samples was an ellipse with major and minor axes of 2 mm and 1 mm, respectively.

In the above-noted second prototype XRD/XRF instrument 100, the time resolution was limited by the readout rate (~2 seconds) of the commercial X-ray CCD 120 and the fact that each frame must be exposed for a period significantly longer (~10 seconds) than the readout rate to reduce contamination of images by "misplaced charge." Misplaced charge is the effect of having photons land physically in the correct part of the device, but during the readout, so that in the final image the registered charge is smeared along the readout direction. The effects of misplaced charge are evident in, for example, the data shown in FIG. 11b. The misplaced charge due to readout rate may be improved by using faster CCD devices, or other technologies (e.g. event driven CCD).

In the data samples described below, the CCD 120 is kept in a vacuum chamber (i.e., housing 101 in this example) with the X-ray source 110. The CCD 120 of the prototypes is chilled, but room temperature X-ray CCDs are expected to become available in the near future and are expected to be utilized in other implementations of the present concepts. For convenience, as shown in FIG. 2b, the sample 126 is kept in air and the X-ray window 145 (e.g., a 0.003" thick Beryllium sheet) separates the vacuum volume inside housing 101 from the exterior environment. As noted above, a shade 157 is provided at the distal end of the collimator 155 to block X-rays diffracting and fluorescing from the window 145. In a third prototype, currently nearing completion and represented generally by FIG. 2c, the X-rays diffracted and fluorescing from the X-ray window 145a (e.g., Beryllium) are virtually eliminated by providing a second, separate window 145b as any X-rays diffracted and fluoresced from the window 145a are not incident to the CCD 120. In the illustrated configuration of FIG. 2c, the CCD is disposed at an angle $\theta_C$ of about 10° to capture a larger range of diffraction angles. The XRD/XRF instrument 100 represented in FIG. 2c provides a geometry allowing work at large d-spacings and is expected to improve the efficiency of the system by allowing the X-rays to pass through windows at nearly normal incidence, which minimizes absorption.

Example 1

AL 6061

Figure 7A:
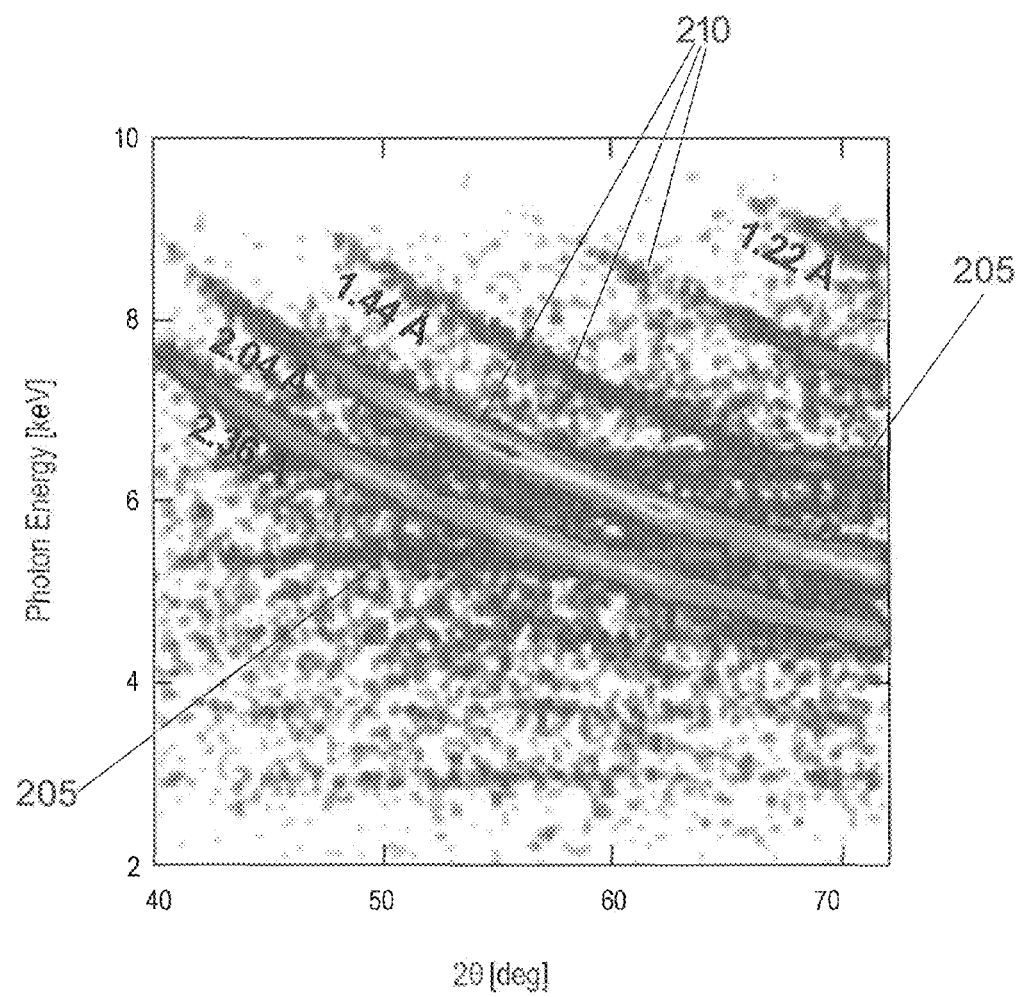

FIGS. 7a-7e show results from a piece of aluminum-6061 obtained using the second prototype XRD/XRF instrument 100 in a 2-hour data run with the X-ray source 110 operating at an electron beam current of 100 microamps. FIG. 7a shows a density plot of the photon count intensity binned in the plane of event energy vs. event diffraction angle. In this space, photons which are due to XRF (e.g., due to contaminants in this case) appear as horizontal lines 205, as shown, and photons due to XRD from crystallized regions with discrete atomic plane spacings (Miller indices) appear as arcs 210, as shown, and trace out Bragg's law for n=1. After applying Bragg's law to compute d-spacing for individual photons, the XRD arcs 210 of FIG. 7a are straightened out as vertical lines 211 in FIG. 7b, while the horizontal XRF lines 205 of FIG. 7a remain as horizontal lines 206. The XRD feature apparent at 1.73 Å is an instrument feature.

In each of FIGS. 7a-7b, several of the XRD arcs 210 and vertical lines 211, are labeled to show some of the expected (tabulated) and detected diffraction features due to aluminum, particularly showing the d-spacings of 1.22 Å, 1.44 Å, 2.04 Å, and 2.36 Å. These arcs 210 sweep from the upper left downwardly toward the lower right with increasing 2θ and represent constant d-spacing. From equations 2 and 14, it can be seen that the energy (E) of the events must decrease with increasing angle for a constant d-spacing. FIGS. 7a-7b are also labeled to show the fluorescence features expected from trace elements in aluminum-6061 (e.g., Fe Kβ, Fe Kα, Cr Kβ, Cr Kα, Ti Kα). FIGS. 7c-7d show how the event data can yield fluorescence (FIG. 7c) and diffraction (FIG. 7d) histograms. The diffraction histogram of FIG. 7d shows that the d-spacing arcs are of differing intensities. It can also be seen that the d-spacing arcs in FIGS. 7a and 7b are broken up in intensity. This is due to a distribution of crystal grain size and planar orientations.

Figure 7E:
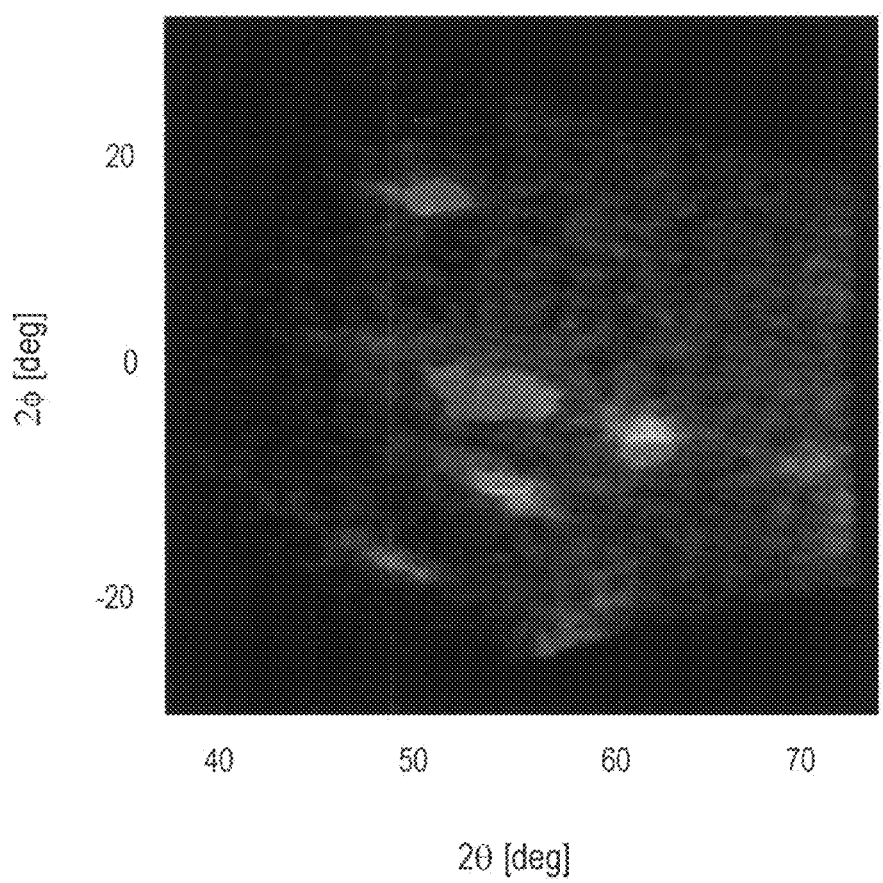

FIG. 7e is a three-color image of diffracted X-ray intensity, in angular coordinates, showing the result of extracting events from the three brightest d-spacing arcs for the aluminum sample in FIGS. 7a-7b (i.e., the arcs corresponding to the d-spacings of 1.44 Å, 2.04 Å, and 2.36 Å), or equivalently the vertical features for the corresponding d-spacing values, and plotting the selected X-ray event locations on the CCD 120, converted to angular coordinates representing the tip-tilt orientations of the crystallite planes. Given the selected d-spacing values and their tabulated correspondence to specific Miller indices (hkl), FIG. 7e depicts the orientations and sizes of crystallite lattice planes (hkl)=(111) (red), (200) (green), and (220) (blue). Thus, FIG. 7e shows the specular reflections off of crystal facets within the illuminated X-ray spot on the sample surface and the image can be analyzed to give detailed information about these facets, as well as gross distributions.

Example 2

Mineral Identification

Figure 8:
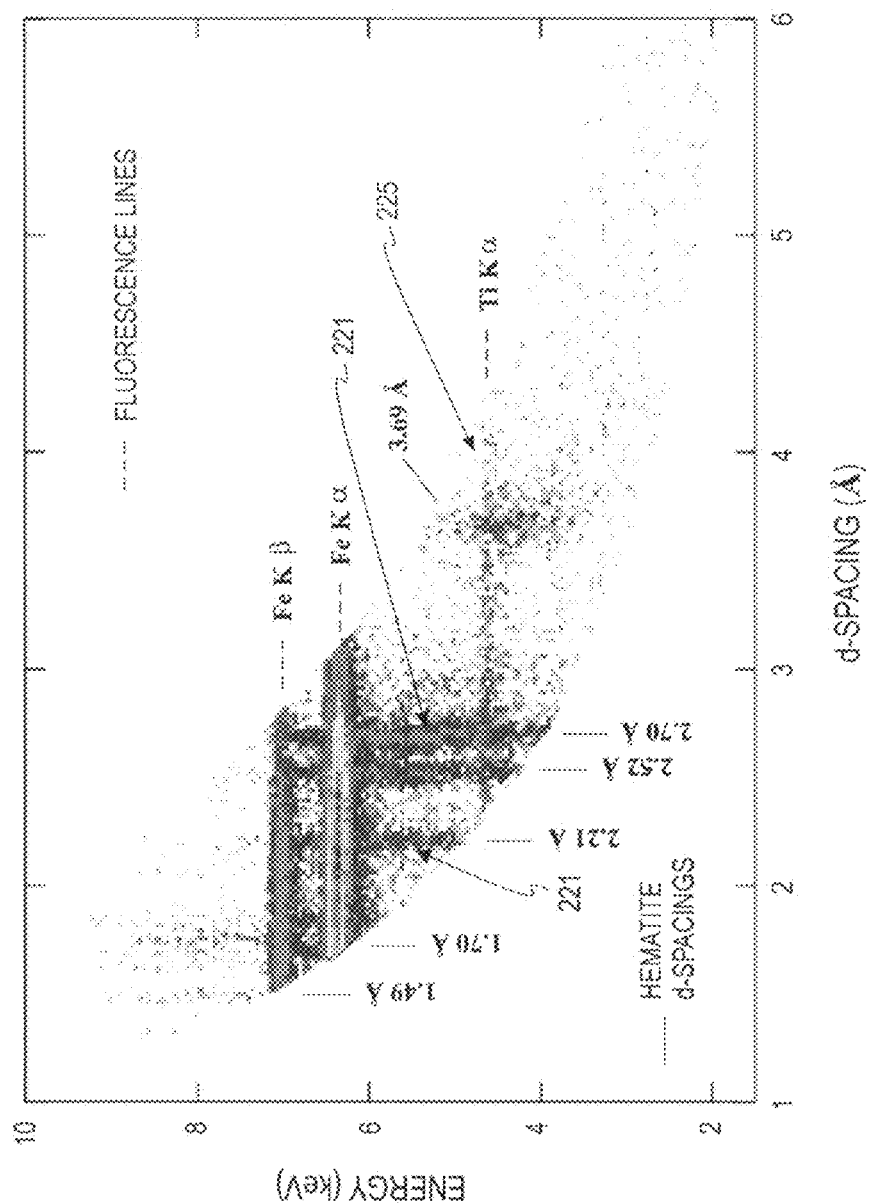
FIG. 8 shows data from a bulk sample of hematite obtained using a prototype XRD/XRF instrument in accord with at least some aspects of the present concepts.

FIG. 8 shows data from a bulk sample of hematite showing both diffraction and fluorescence features. As with FIG. 7b, the hematite data is binned and plotted in the space of energy (E) vs. d-spacing, as shown in FIG. 8. XRD data is shown as vertical lines 221, while the XRF data is shown as horizontal lines 225. FIG. 8 is labeled to show some of the expected and detected diffraction features, particularly showing the d-spacings of 1.49 Å, 1.70 Å, 2.21 Å, 2.52 Å, and 2.70 Å. A faint d-spacing vertical line is also observable at 3.69 Å. FIG. 8 is also labeled to show the expected fluorescence features (e.g., Fe K$\beta$, Fe K$\alpha$, and Ti K$\alpha$).

Because d-spacing information acts as an effective "fingerprint" for any given mineral, the specific combination of vertical features 221 in FIG. 8 can be used to identify the sample. D-spacing values for thousands of organic and inorganic substances are available in commercial and freely available digital databases (e.g., www.webmineral.com), and the process of reducing data obtained by the XRD/XRF instrument 100 to identify minerals present in pure or mixed-phase samples lends itself to automation. Mineral identification algorithms based on matched filtering techniques are especially promising, as elemental composition from fluorescence reduces the number of tabulated minerals for which d-spacings must be matched to the sample.

"Rietveld refinement" (e.g., Bish & Howard 1988) of a one-dimensional diffractogram is the most common means of determining a sample's constituent minerals. The technique consists of fitting for the intensities and widths of diffraction peaks given expected crystal structures present in the sample. Although best suited to powders, the method allows for moderate preferred-orientation effects, which are likely in unprepared samples. The Rietveld treatment is least reliable when a small number of specular reflections contributes most of the flux in a diffraction peak, but in these instances the multiwavelength approach of the XRD/XRF instrument 100 and techniques described herein allows measurement of the number, sizes, and orientations of the crystallites, quantities that are normally unknowns for which the Rietveld formulae attempt to find best-fit values as an intermediate step.

The use of the Rietveld technique as a tool for surface analysis of bulk samples is presently under study. It appears that the diffraction profile produced by an X-ray spot of about 1 mm in diameter illuminating a multi-phase, rocky sample is typically uncomplicated, with dominant d-spacings unique to just one or two minerals at a given position on the sample. Scanning the surface, or abrading it to expose sub-surface layers and collecting new X-ray data, then provides information about minor accompanying phases. It is therefore believed likely that a combination of Rietveld analysis, "bootstrapping" the dominant crystal phases, and judicious examination of bulk samples will readily reveal mineral content.

The high resolution d-spacing measurement resolution achievable with the XRD/XRF instrument 100 disclosed herein permits accurate mineral identification and enables the identification of different mineral phases within a sample.

Example 3

Aerosol Identification

Applications involving aerosols require a high detection limit to measure trace elements and require high sensitivity to permit analysis of minute amounts of material. A typical aerosol filter configured to collect particles on its surface (e.g., the Nuclepore® filter) holds about 20 µg/cm$^2$ of aerosol mass. For a X-ray beam 105 having a spot size area of about 2 mm$^2$, which is the case for the current example, the total aerosol mass observed by the beam is about 0.4 µg.

FIGS. 9a-9c show an example of an aerosol filter, analyzed using the disclosed XRD/XRF instrument 100 and techniques disclosed herein, showing measurements of at least 9 elements with X-ray fluorescence and identifying at least three major minerals in the analyzed sample (i.e., calcite, hematite, and halite). The aforementioned second prototype of the XRD/XRF instrument 100 (see generally FIG. 2b) was used to analyze data from micrograms of dust collected on a thin polycarbonate Nuclepore® filter. Single-photon events detected by the CCD 120 are binned in energy (E) and d-spacing. Colors in FIG. 9a represent binned intensities as shown on the inset scale. Horizontal features 240 result from X-ray fluorescence and vertical features 241 result from X-ray diffraction, as previously noted. FIG. 9a shows, among other X-ray fluorescence features 240, twelve measured or expected X-ray fluorescence features including Fe K$\beta$, Fe K$\alpha$, Mn K$\alpha$, Ti K$\alpha$, Ca K$\beta$, Ca K$\alpha$, K K$\alpha$, Ar K$\alpha$(air), S K$\alpha$, Cl K$\alpha$, P K$\alpha$, and Si K$\alpha$. The brightest XRF features have been excised from the data corresponding to FIG. 9a to form the d-spacing spectrum shown in FIG. 9b. FIG. 9b shows, for example, a Beryllium d-spacing at about 1.73 Å, due to the Beryllium window, calcite d-spacings at 2.10 Å, 2.28 Å and 3.04 Å, Hematite d-spacings at 2.51 Å and 2.69 Å, and a Halite d-spacing at 2.82 Å. FIG. 9c shows a photon energy spectrum for the data in FIG. 9a.

The outstanding sensitivity that allows for such analysis arise from the combination of the favorable geometry, the large detector cross section, the low noise/high sensitivity photon counting detector, and especially the simultaneous measurements at many different scattering angles, made possible by the use of a broadband X-ray source, provided by the XRD/XRF instrument 100 and techniques disclosed herein.

The aerosol analysis can be performed in several different modes. Three non-limiting modes are described below. First, filters may be collected in the field and saved for later analysis in a laboratory. Second, real-time or automated filter or impactation systems may be used to provide sampling and analysis directly in the field. For example, aerosol sampling and analysis can be performed automatically with the disclosed XRD/XRF instrument 100 and techniques in combination with another modality where the particles are sampled on a moving tape system that allows the sampled spot to move in front of the XRD/XRF instrument window for analysis, such as is shown by way of example in FIG. 5a. Third, aerosol analysis may be performed in a real-time, "flyby" system where the aerosols (e.g., ice or other types of particles) are analyzed while still in suspension in the atmosphere, such as is shown by way of example in FIG. 5b. In this geometry, particles passing in the right geometry (i.e., a predefined volume about a known coordinate 125 ($x_0$, $y_0$, $z_0$)) in front of the window are flagged by a laser tagging system (e.g., laser scattering to a photodiode or photodiode array positioned in a geometry to see scattered photons coming from that particular volume). In at least some aspects, such predefined volume may comprise a volume of about 100×100×100 $\mu m^3$. In other aspects, the predefined volume may be larger or smaller.

Example 4

Volatiles Identification

Because the disclosed XRD/XRF instrument 100 and techniques do not require sample preparation, they can be used to analyze volatiles, such as water ice, which may evaporate if prepared for a conventional d-spacing XRD analysis. This particular aspect of the present concepts is particularly important for space exploration applications of the XRD/XRF instrument 100, where powdering of water ice in a low pressure environment would cause the ice to evaporate and evidence thereof would be lost.

Figures 10A, 10B:
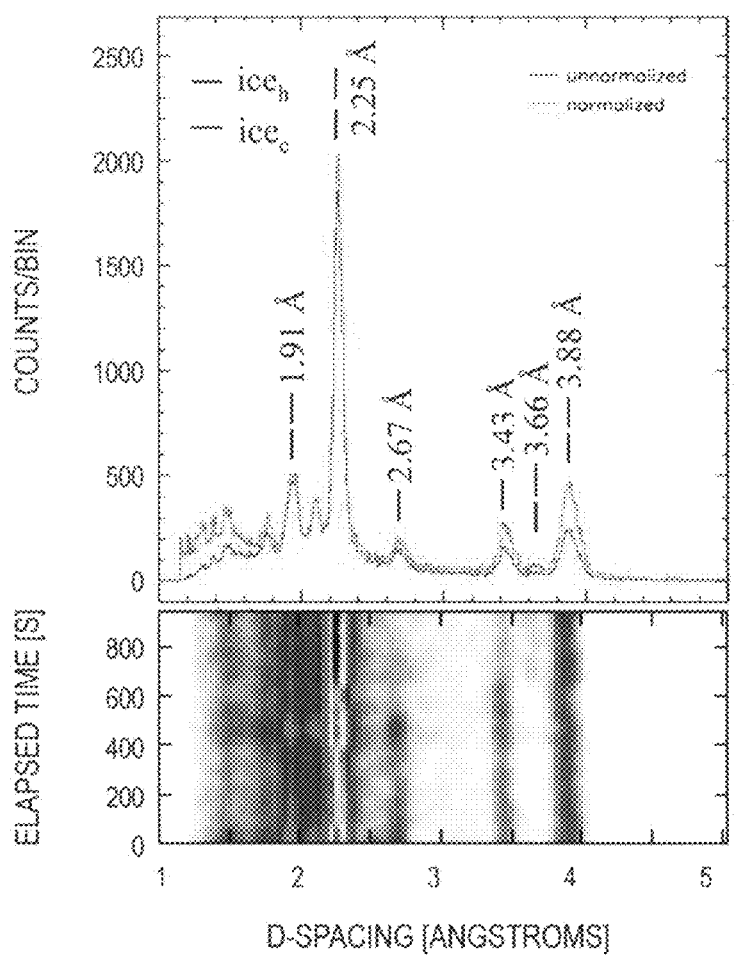
FIGS. 10a-10c show data from a volatile sample obtained using a prototype XRD/XRF instrument in accord with at least some aspects of the present concepts.
Figure 10C:
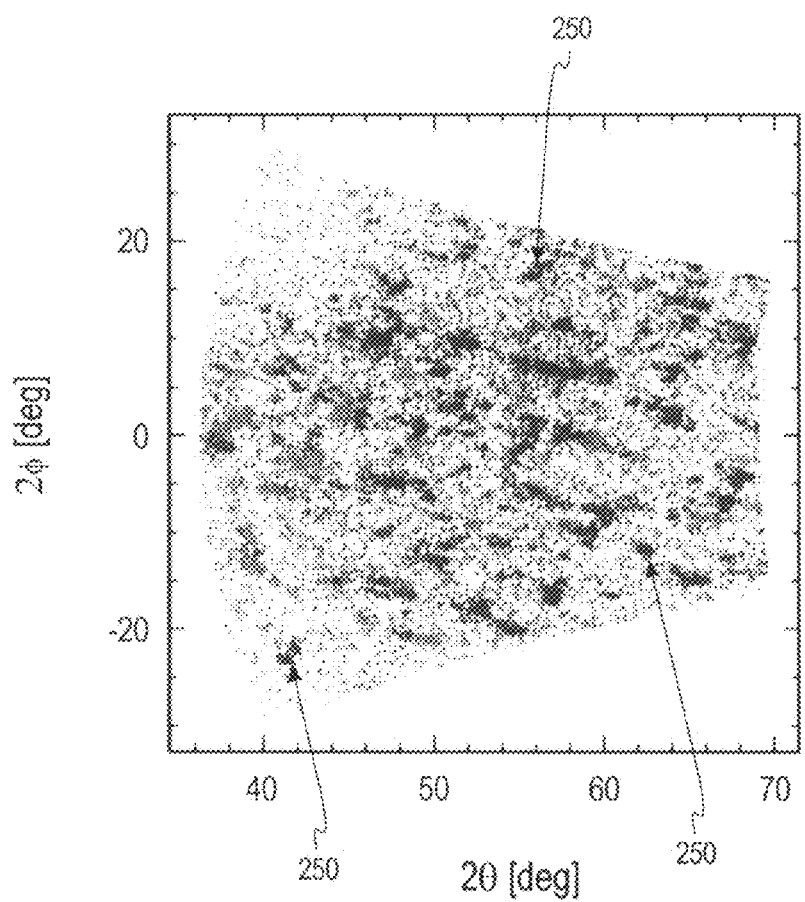

FIG. 10a-10c show diffraction data for frost accumulated on the outside wall of a plastic receptacle containing liquid nitrogen. In FIG. 10a, known d-spacings from hexagonal ice ($ice_h$) and cubic ice ($ice_c$) (e.g., peaks for $ice_h$ at 1.91 Å, 2.25 Å, 2.67 Å, 3.43 Å, 3.66 Å, and 3.88 Å and peaks for $ice_c$ at 1.91 Å, 2.25 Å, 3.66 Å, and 3.88 Å) observed in a diffraction spectrum. The image in FIG. 10b shows the time-dependence of the observed d-spacings and maps changes in the diffraction peaks with time over a 15-minute interval. Up to six diffraction peaks are visible in a single 10-sec exposure, and there is evidence of a change at roughly the 10-minute mark wherein the diffraction peak at 2.25 Å grows stronger (i.e., darker or red to black in FIG. 10b) while a new peak at 3.66 Å begins to emerge. At the same time, the peaks at 2.07 Å and 2.67 Å appear to fade. Such analysis of rapidly time-dependent phenomena is virtually impossible with existing XRD instrumentation.

FIG. 10c shows a scatter-plot of individual photons distributed in angular diffraction coordinates, where color refers to different d-spacings of 1.91 Å (red), 2.25 Å (blue), 3.43 Å (deep sky blue), and 3.88 Å(magenta). FIG. 10c shows numerous distinct spots 250, which are diffraction features (i.e., specular reflections), from frost grains of a few hundred microns in size. The spots 250 in FIG. 10c provide important texture data, which permits determination of the actual size of the frost grains causing the specular reflections based on the geometry of the XRD/XRF instrument 100 (e.g., the known angular relation between the X-ray source 110 and the photon-counting X-ray imaging spectrometer, such as CCD 120)). This texture data, which also includes the location of the spot 250 (i.e., the tip-tilt of the frost grain) cannot be obtained from prepared samples, which destroys such crystalline texture data.

Example 5

Organic Crystal Identification

The disclosed XRD/XRF instrument 100 and techniques are also ideally suited for X-ray crystallography, the technique of choice for determining the molecular structures of organic compounds, including proteins that are vital for pharmacological studies. One simple organic crystal is common sugar, or sucrose.

The XRD/XRF instrument 100 and techniques disclosed herein provide novel benefits for crystallographic analysis. Traditional techniques for deriving crystal structure by inverting Laue patterns, collected without single-photon spectroscopy, are applicable to data obtained by the XRD/XRF instrument 100, with the added enhancement that CCD 120 spectroscopy provides identifiable d-spacings for all observed Laue spots, even for a broad continuum energy band. Because the larger bandwidth samples previously unseen atomic plane orientation, the disclosed XRD/XRF instrument 100 can yield improved Laue inversions. Further, the high energy resolution of CCDs 120 should be sufficient to allow for new implementations of the "multi-wavelength anomalous dispersion" technique for solving the "phase problem" in deriving crystal structures.

Figure 11B:
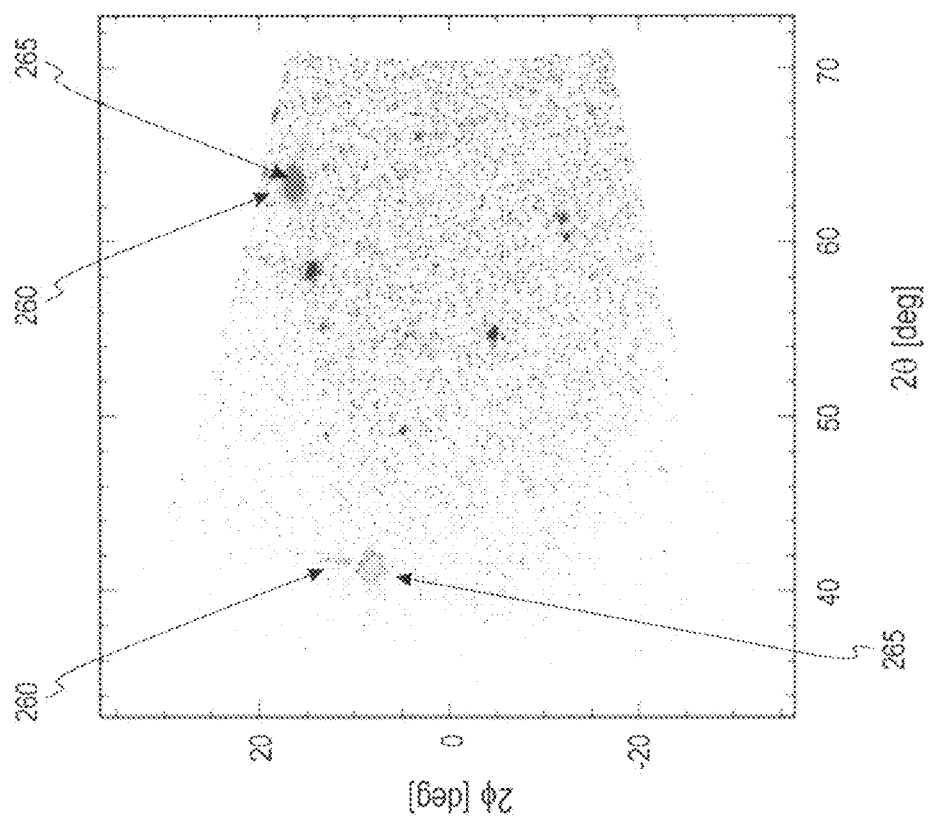
FIGS. 11a-11b show data from an organic crystal obtained using a prototype XRD/XRF instrument in accord with at least some aspects of the present concepts.
Figure 11A:
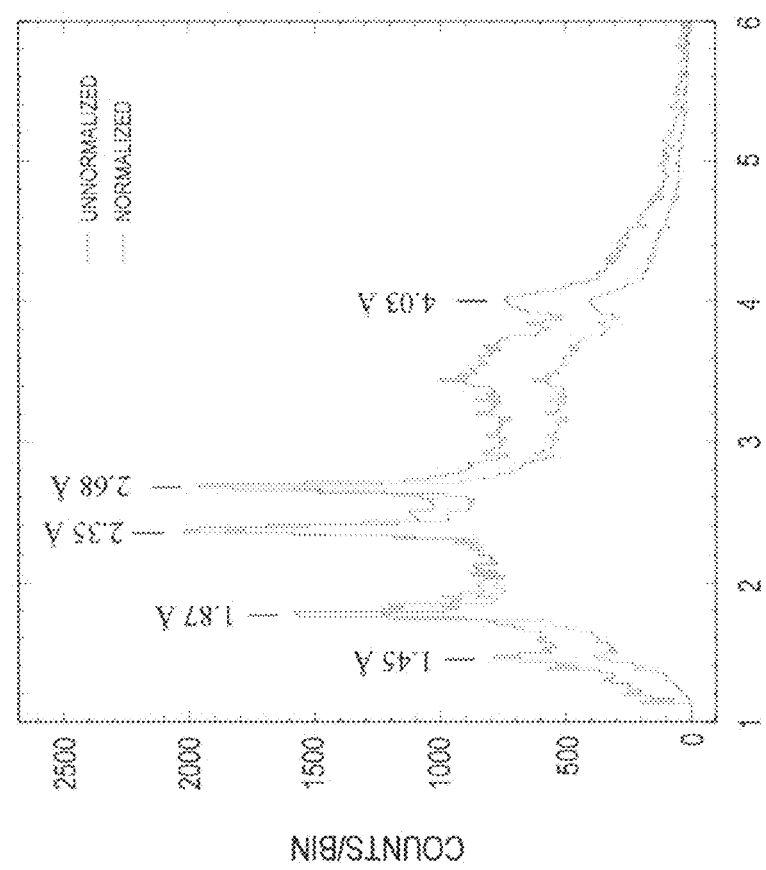

FIGS. 11a-11b display data for a single sugar crystal, roughly 200 microns on a side, obtained using the disclosed second prototype of the XRD/XRF instrument 100 over a period of about 3 hours. FIG. 11a shows a diffraction spectrum exhibiting known d-spacings of sucrose (e.g., peaks at about 1.45 Å, 1.87 Å, 2.35 Å, 2.68 Å, and 4.03 Å). FIG. 11b shows a diffraction pattern for the single-crystal of sucrose. In FIG. 11b, the diffraction pattern comprises Laue spots from distinct Miller indices corresponding to the color-coded d-spacings of 1.45 Å (red), 1.87 Å (blue), 2.35 Å (deep sky blue), 2.68 Å (magenta), and 4.03 Å (yellow).

In panel FIG. 11a, the sharp diffraction peaks for the d-spacings of 1.45 Å, 1.87 Å, 2.35 Å, 2.68 Å, and 4.03 Å sit on top of a much broader feature, which is due to scattering from largely amorphous Kapton, used as a membrane to hold the sugar crystal in the X-ray beam 105. In FIG. 11b, it may be observed that streaks 260 arc clockwise from the two brightest Laue spots 265. These streaks 260 are indications of misplaced charge. The misplaced charge arises in this prototype data because the specular reflections are bright enough that, as the CCD 120 reads out, photons continue to strike the detector, producing blurring along the readout direction. In future embodiments, these streaks may be minimized or eliminated by using CCDs with much faster readout times (e.g., less than about 1 second or, still better, less than 100 milliseconds) and/or frame-transfer regions. Alternatively, the X-ray source flux could be reduced in special cases where there are bright Laue spots.

The prototype data shown above in FIGS. 7a-11b, together with the integration times necessary to achieve the evident signal-to-noise ratios, allow for robust estimates of the sensitivity that can be achieved by improving system components. Anticipated sensitivity gains through improvements in component technologies and systemic optimizations are discussed below. The total gain for the estimated improvements in sensitivity gain factor for further component and system improvements is expected to be about 10,000. It is noted that the aerosol data shown in FIGS. 9a-9c required a 17-hour integration. It is estimated that future implementations of the present concepts implementing the following improvements will be able to replicate this dataset in a minute or less.

First, the deep-depletion CCD 120 for single photon X-ray spectroscopy may be improved by providing a larger collecting area, better energy resolution, higher quantum efficiency, a frame-store region, and a portable, low-noise readout. The larger collecting area provides a larger d-spacing range and/or increased sensitivity by collecting more of the Debye arcs (in continuum) for diffracted rays, producing an estimated sensitivity gain factor of about 2.0. A better energy resolution would sharpen peaks in XRF and XRD spectra by about 50% to resolve closely-spaced features and boost S/N, producing an estimated sensitivity gain factor of about 1.2. A higher quantum efficiency broadens the range and resolution of XRD spectra, as well as the sensitivity to high-energy XRF lines (e.g., heavy metals in pollution aerosols) and is estimated to increase the sensitivity gain factor by about 1.2. The frame-store region would rapidly transfer charge from the illuminated CCD area, obviating need for a shutter and eliminating misplaced charge (small S/N gain) and is estimated to increase the sensitivity gain factor by about 1.1. The portable, low-noise readout is not estimated to increase the sensitivity gain factor, but will render thermo-electric cooling (TEC) sufficient, allowing for a lightweight field unit.

Improvements are also contemplated for the X-ray source 110 itself. By providing X-Ray Optical Systems (XOS® (of East Greenbush N.Y., USA)) polycapillary optics, it is possible to capture much larger solid angle of X-rays emitted by the source anode, significantly boosting flux relative to pinhole collimator, which flux is then guided to an aperture of chosen diameter. It is estimated that this improvement will alone increase the sensitivity gain factor by about 500, depending on the chosen aperture diameter. A higher beam current is further estimated to increase sensitivity gain factor by about 5 by increasing the continuum X-ray flux. A higher accelerating potential is also estimated to increase sensitivity gain factor by about 1.2 by increasing continuum X-ray flux, range of d-spacings, and likelihood of exciting XRF at higher energies. Still another improvement to boost the sensitivity gain factor includes alteration of the overall system geometry and vacuum windows to optimize CCD placement and window material. These improvements should broaden XRD range toward large d-spacings, increase sensitivity to XRF features below 2 keV, and reduce the aforementioned instrument features.

In the above-described XRD/XRF instrument 100 prototype data for the aerosol and frost samples, the aerosol and frost samples filled the X-ray beam 105. This is the most efficient use of the available X-ray flux. For particles smaller than the beam, the sensitivity is reduced by the ratio of the areas of particle to beam. To mitigate this degradation, additional embodiments of our present concepts may advantageously utilize polycapillary optics, which will produce a net flux gain while focusing the X-rays to a chosen spot size (e.g., as small as 200 microns for parallel rays, or 10 microns in slightly converging rays) to allow for in-situ analysis of the smallest sample particles without intolerable loss of sensitivity. It may be conservatively estimated that a 200-micron beam on a 10-micron particle will result in an overall sensitivity gain of a factor of 20. For the smallest particles, there will also be a loss term due to transmission through the particle without an XRF or XRD interaction. At the photon energies that will often be employed in combination with the disclosed XRD/XRF instrument 100, this loss term will amount to a factor of 2 loss, so that the net sensitivity gain is still an order of magnitude (i.e., a gain of 10). With the frost data discussed above in relation to FIGS. 10a-10c, six d-spacing XRD features were detected in a single 10-sec frame. Given the factor of 10 sensitivity boost, a high-sensitivity XRD/XRF instrument 100 should allow this same level of statistical significance for a single 10-micron ice crystal in the same time or less.

Although the combined use of (1) a continuous spectrum of X-rays, and (2) the geometry of reflection, instead of transmission, is discussed herein in relation to certain of the embodiments and aspects disclosed herein, together with attendant benefits flowing therefrom with respect to the disclosed XRD/XRF instrument 100 and the disclosed methods or acts, the disclosed XRD/XRF instrument 100 as well as the disclosed methods or acts may be utilized in combination with a transmissive geometry and/or a prepared sample. For example, certain of the disclosed XRD/XRF instrument 100, methods, or acts, to the extent not logically prohibited, may use a thin sample, prepared or unprepared (e.g., single crystal), and transmit an X-ray beam (e.g., 105) from the X-ray source (e.g., 110) through the thin sample. FIGS. 12a-15b, discussed below, schematically show the types of data that would result from four potential combinations of instrument type (single-wavelength in FIGS. 12a-12b and 14a-14b, multi-wavelength in FIGS. 13a-13b and 15a-15b) and sample preparation (powdered in FIGS. 12a-12b and 13a-13b, unprepared in FIGS. 14a-14b and 15a-15b). In other words, the series of plots represented in FIGS. 12a-12b through 15a-15b show a comparison of the characteristics of some types of data obtained using an XRD/XRF instrument 100 in accord with the present concepts and the data obtainable using other XRD/XRF instruments 10, such as that shown in FIG. 1, under the same conditions.

Figure 12B:
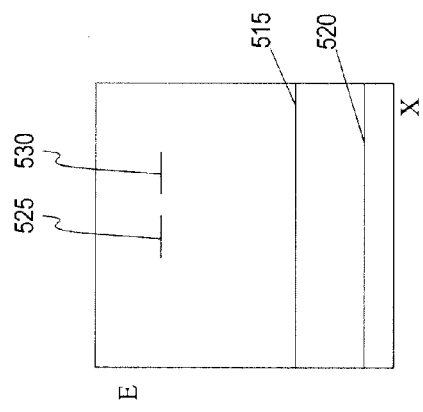
FIGS. 12a-12b represent data that could be expected to be obtained from a powdered sample using a conventional single-wavelength XRD/XRF instrument.
Figure 13B:
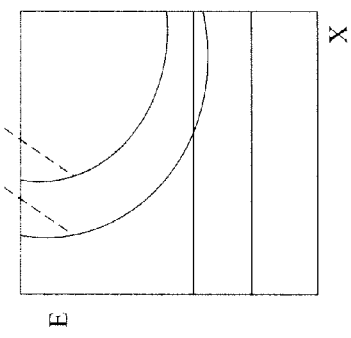
FIGS. 13a-13b represent data that could be expected to be obtained from a powdered sample using a multi-wavelength XRD/XRF instrument in accord with at least some aspects of the present concepts.
Figure 12A:
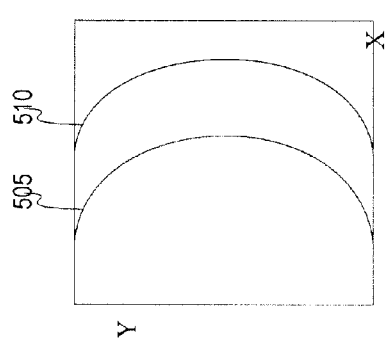
Figure 13A:
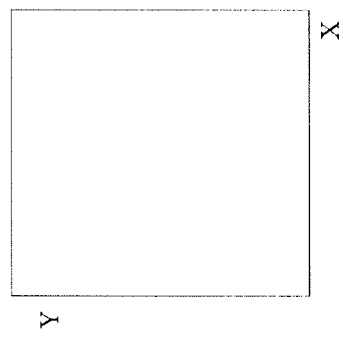

FIGS. 12a and 13a show schematically in a CCD Y-position vs. X-position plot the types of data that would result from the XRD/XRF instruments 32, 100 (i.e., single-wavelength vs. broad spectrum, respectively) for a powdered sample. FIGS. 12b and 13b show schematically in an energy vs. X-position plot the types of data that would result from the XRD/XRF instruments 32, 100 (i.e., single-wavelength vs. multi-wavelength, respectively) for a powdered sample.

FIG. 12a shows the traditional configuration for X-ray diffractometry wherein a single-wavelength XRD/XRF instrument 32 is used on a powdered sample. The addition of an energy-dispersive detector, such as CCD 46 shown in FIG. 1, allows for simultaneous fluorescence spectroscopy, but with potentially poor efficiency because of the potential for mismatches between the single input X-ray energy and the characteristic lines of elements in the sample. Diffracted X-rays striking the CCD 46 form arcs 505, 510 in the image (X-Y) plane. These arcs 505, 510, known as Debye rings, arise because the orientations of crystal grains ("crystallites") in the sample have been randomized by the powdering of the sample. However, the powdered sample lacks texture (i.e., a non-random distribution of crystallographic orientations of a sample) since the processing of the sample for XRD/XRF analysis seeks to eliminate any preferred orientation of the crystallites. Thus, valuable texture information, which can be an important factor in understanding the mechanical, physical and/or chemical behavior of the sample, is lost.

FIG. 12b shows the registering of event energies on CCD 46 in the form of a scatter plot of energy (E) vs. X-position. Specifically, FIG. 12b shows X-rays emitted through fluorescence as horizontal lines 515, 520, while the diffraction arcs 505, 510 in FIG. 12a are shown to collapse to short segments 525, 530 in X at the fixed energy of the X-ray source. The distribution of the horizontal fluorescence lines 515, 520, is essentially independent of position.

FIGS. 13a-13b represent plots for a configuration wherein the broad spectrum XRD/XRF instrument 100 in accord with aspects of the present concepts outputs a continuum spectrum of X-rays onto a powdered sample. In FIG. 13a, fluorescence of the sample produces X-rays that are distributed isotropically (i.e., directionally invariant) over the detector (e.g., CCD(s) 120), while diffracted rays strike the detector at a wavelength ($\lambda$) and angle ($\theta$) satisfying Bragg's law. Because the X-ray source produces a continuum spectrum of wavelengths, and the powdered sample contains a continuum of crystallite orientations that determine θ, the resulting distribution of diffracted photons on the imaging surface of the CCD(s) 120 is also virtually isotropic, resulting in a generally featureless image. In the energy (E) vs. X-position plot of FIG. 13*b*, the diffraction events forming arcs 540, 545 reflect individual d-spacings of the sample, consistent with Bragg's law. Individual arcs arising from distinct d-spacings can be resolved as permitted by the energy resolution and spatial resolution capability of the CCD(s) 120 As in FIG. 12*b*, fluorescence events in FIG. 13*b* appear as horizontal lines.

Figure 14A:
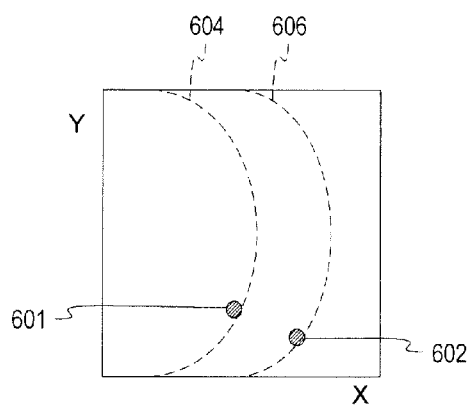
FIGS. 14a-14b represent data that could be expected to be obtained from an unprepared sample using a conventional single-wavelength XRD/XRF instrument.
Figure 14B:
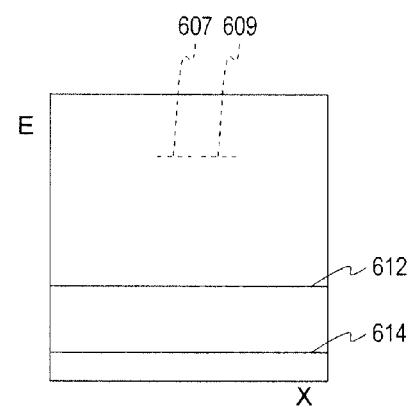
Figure 15A:
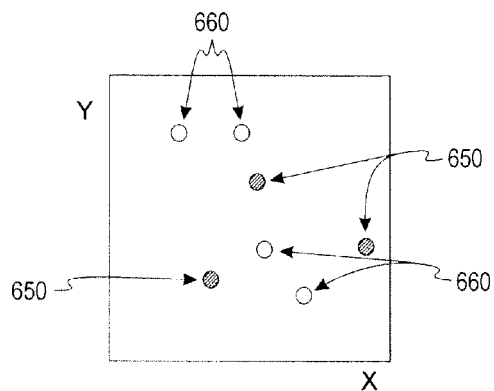
FIGS. 15a-15b represent data that could be expected to be obtained from an unprepared sample using a multi-wavelength XRD/XRF instrument in accord with at least some aspects of the present concepts.
Figure 15B:
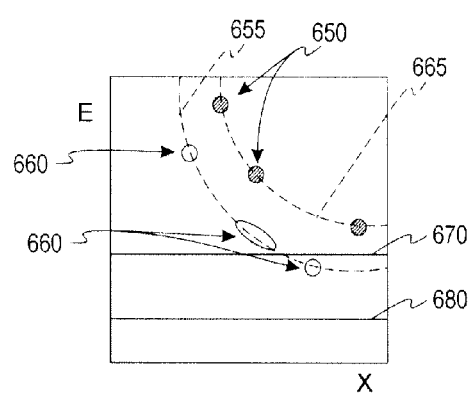

FIGS. 14*a* and 15*a* show schematically in a CCD Y-position vs. X-position plot the types of data that would result from the XRD/XRF instruments 32, 100 (i.e., single-wavelength vs. broad spectrum, respectively) for an unprepared sample. FIGS. 14*b* and 15*b* show schematically in an energy vs. X-position plot the types of data that would result from the XRD/XRF instruments 32, 100 (i.e., single-wavelength vs. broad spectrum, respectively) for an unprepared sample.

FIG. 14*a* shows a representation of a CCD Y-position vs. X-position plot for a conventional single-wavelength XRD/XRF instrument 32 (see, e.g., FIG. 1) used on an unprepared sample. This is the worst-case scenario for traditional XRD studies. Unlike powdered samples, the orientations of crystallites in an unprepared sample are potentially highly-aligned or, in a pure single crystal, strictly aligned. Thus, diffracted rays may be preferentially oriented in a single direction. If the detector (e.g., CCD 46 of FIG. 1) does not cover a sufficient solid angle to intercept the diffracted ray, that ray will be missed, resulting in the loss of valuable d-spacing information. For this reason, traditional diffractometers 32 are designed so that the detector is mounted on a movable stage (or, equivalently, the sample is placed on a rotating holder, a goniometer). As previously noted, these moving parts reduce the reliability of the device and substantially increase the time it takes to acquire data at many angles, which is required for crystallographic studies. If some crystallites are fortuitously aligned with a stationary detector, some diffracted flux will be measured in certain locations, producing "splotches" 601, 602 along the same arcs that would have resulted from a powdered sample. In FIG. 14*a*, the dashed curves 604, 606 represent these undetected arcs. FIG. 14*b* shows fluorescence events as horizontal lines 612, 614. FIG. 14*b* also shows that any X-rays producing "splotches" 601, 602 would appear as points or short segments 607, 609 in X at the fixed energy of the X-ray source.

FIG. 15*a* shows a representation of the use of the broad spectrum XRD/XRF instrument 100 in accord with aspects of the present concepts on an unprepared sample. Because the X-ray source (e.g., 110 in FIG. 2*b*) outputs a range of X-ray wavelengths, diffracted X-rays satisfying Bragg's law (shown as different shades of gray in FIGS. 15*a*-15*b* for different d-spacings) from pure crystals are virtually guaranteed to strike the stationary detector (e.g., CCD 120 in FIG. 2*b*). In the image plane (Y-X plane) of FIG. 15*a*, one or more splotches 650, 660 will appear depending on the ratio of crystallite size to the size of the illuminated X-ray beam 105 spot on the sample surface. If many small crystallites of a given d-spacing and having arbitrary orientation are illuminated, their diffracted outgoing X-rays will produce a pattern of splotches 650, 660 through specular reflection that contains valuable information about the crystalline texture. In the E-X plane, the events corresponding to the splotches 650, 660 are constrained by Bragg's law to lie on constant d-spacing arcs 655, 665, while fluorescence lines 670, 680 are again distinguished because their energies do not depend on event position on the CCD 120.

The use of a continuous spectrum of X-rays in combination with a geometry of reflection, instead of transmission, provides at least some of the benefits described herein. For example, although both the broad spectrum XRD/XRF instrument 100 (see generally FIGS. 2*a*-15*b*) and the conventional XRD/XRF instrument 32 both detect diffracted X-rays from forward-scattered cones emanating from the sample, the broad spectrum XRD/XRF instrument 100 typically examines the sample in a reflection geometry, while the conventional XRD/XRF instrument 32 requires, without exception, transmission of X-rays through the sample. Two immediate consequences follow. Because X-rays of a few keV in energy penetrate only tens of microns in typical minerals, this determines the maximum thickness of a sample and correspondingly requires the need to grind up the sample into a powder of sufficient fineness to permit transmission of X-rays through the sample. Unfortunately, such handling destroys valuable information originally contained in the sample about crystal grain sizes and the orientations of their lattice planes while also releasing volatiles, such as water ice. In a reflection geometry, the low transmission depth means that the analysis is necessarily of surface material, but this is not a disadvantage. Once the surface has been examined, an abrasion tool can be used to remove surface layers and explore within. In each case, the crystal grains and volatiles in the sample remain largely undisturbed.

Further, as previously noted, the transmission configuration of the XRD/XRF instrument 32 in FIG. 1 requires sample material to be transported inside the instrument, resulting in significant mechanical complexity, increased risk of failure or contamination (e.g., of the CCD, or in cross-sample residual powder), and the inability to analyze bulk samples. In the disclosed embodiments of the XRD/XRF instrument 100 utilizing a reflection geometry, the option is available to seal the instrument's sensitive components to prevent direct contact with the sample and, instead of transporting the sample inside the XRD/XRF instrument, the instrument can simply be placed against any surface to obtain comprehensive XRD/XRF analysis.

Still other advantages stem from the disclosed XRD/XRF instrument 100's unique use of continuum spectrum X-rays and the spectroscopic capability of the CCD 120, not only to provide XRF spectra, but to detect the characteristic spatial patterns of diffracted X-rays as well. The disclosed XRD/XRF instrument 100 X-ray source 110 provides an emission spectrum dominated by continuum. For samples containing large, well-ordered crystal grains, diffraction will produce specular reflections of X-rays according to Bragg's law, instead of smooth Debye arcs, and the spatial pattern imaged by the CCD will consist of a number of bright spots. With a fixed detector and limited imaging area, the range of angles sampled in both 2θ and azimuth (i.e., along a Debye arc) is constrained. With monochromatic X-rays, such as with the conventional XRD/XRF instrument 32, the coverage provided by the detector's collecting area limits the range of d-spacings that can be sampled, no matter the orientations of crystal grains in the sample. Worse, for highly organized crystal samples, diffraction peaks may be altogether absent for unfavorable orientations of the lattice planes (e.g., Bragg's law fixes the relationship between d-spacing, the diffracted angle, and the wavelength, resulting in constructive interference from only those crystallites satisfying a particular orientation). The conventional XRD/XRF instrument 32 remedies this situation by powdering the sample to randomize the orientations of the crystal grains and improve the chances that some diffracted rays will strike the detector. However, the improved XRD/XRF instrument 100 and techniques disclosed herein using a range of input X-ray wavelengths provides sensitivity to a much broader range of d-spacings by allowing λ in Bragg's law to vary and by permitting sampling by the detector 120 of a range of 2θ information. Similarly, preferred-orientation effects are minimized, as the chances of a diffraction peak at some wavelength striking the detector are significantly improved. The disclosed XRD/XRF instrument 100 and techniques therefore take full advantage of a CCD's 120 collecting area and spectroscopic capability.

It is noted that, to achieve sufficient angular coverage in a transmission geometry using a monochromatic X-ray beam, such as is used in CheMin, the sample material must be placed very close (a few mm) to the CCD 46. In addition to increased mechanical complexity and risk to the CCD, this geometry requires that the X-ray spot illuminating the sample be very small, about 50 microns. As a result, a highly focused X-ray source would be a fundamental requirement for such conventional XRD/XRF instrument 32. With the disclosed XRD/XRF instrument 100, the sample can be placed 2-3 cm away from the CCD 120 for comparable XRD performance, resulting in looser tolerances on the X-ray source 110 while also allowing a much higher X-ray flux to illuminate the sample. The disclosed XRD/XRF instrument 100 is therefore a faster instrument, providing the same XRD information in much less time than the conventional XRD/XRF instrument 32 given the same X-ray source power.

Further, the use of a broad continuum spectrum of X-rays to illuminate a sample 126 in the disclosed XRD/XRF instrument 100 results in a faster XRF instrument for the reason that atoms fluoresce most efficiently when they are excited by radiation that closely matches their electron-shell transition energies. Monochromatic photons, such as those utilized in the conventional XRD/XRF instrument, cannot efficiently excite transitions in a wide variety of elements. In contrast, in aspects of the disclosed XRD/XRF instrument's 100 having a continuum emission up to about 10-15 keV a good match for all but the highest-Z elements is assured.

Figure 16:
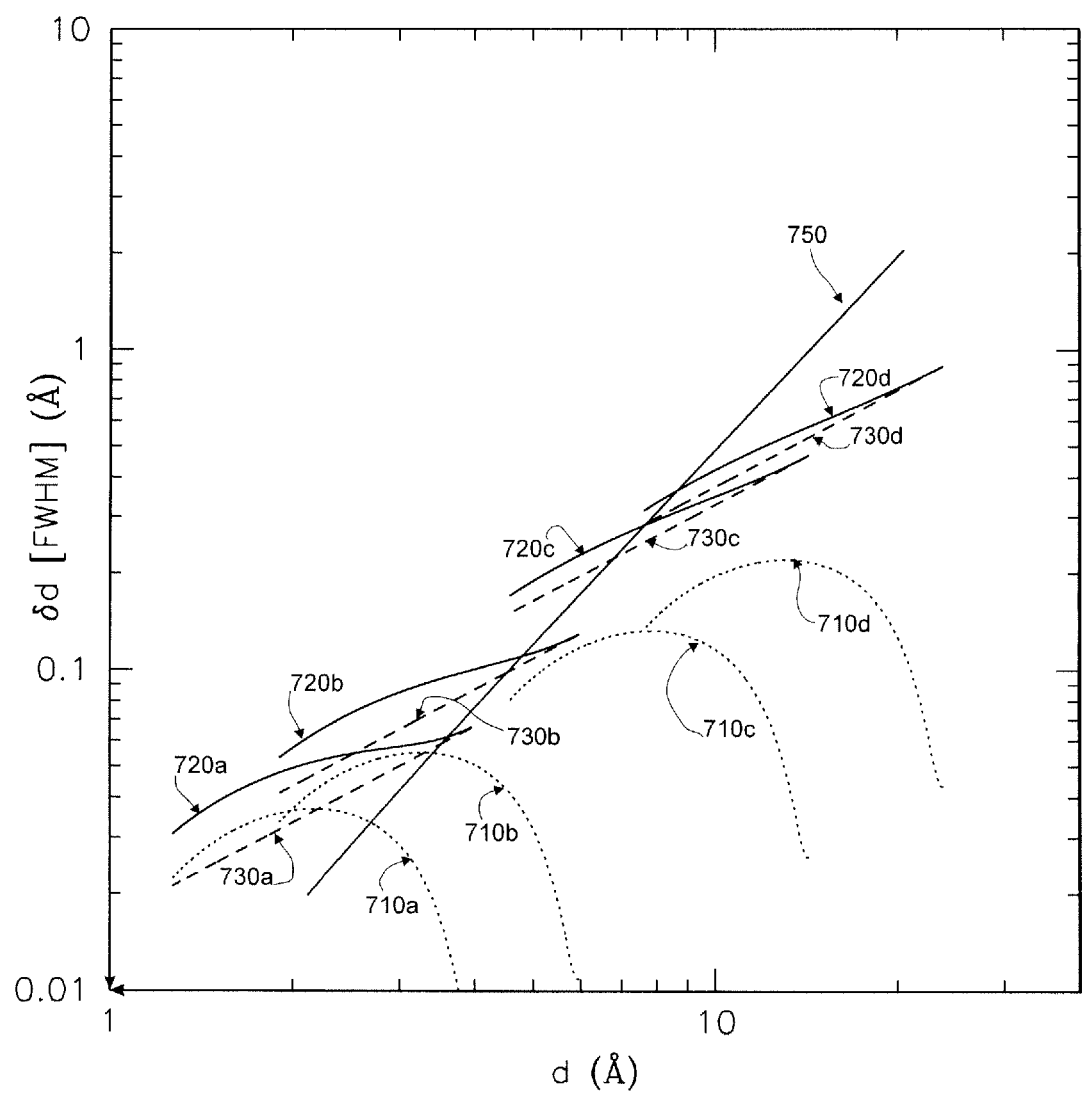
FIG. 16 depicts a comparison between an expected d-spacing measurement resolution and range of the XRD/XRF instrument of FIG. 2c to the XRD/XRF instrument of FIG. 1.

FIG. 16 compares the expected d-spacing measurement resolution (full width at half-maximum of diffractogram peaks) of the disclosed third prototype XRD/XRF instrument 100 (see, e.g., FIG. 2c) to the XRD/XRF instrument 32 (i.e., a monochromatic, transmission-based geometry XRD instrument such as CheMin) shown in FIG. 1. The d-spacing measurement resolution curve of the XRD/XRF instrument 32 for a constant $\delta(2\theta)=0.3°$ is represented by reference numeral 750. For the disclosed XRD/XRF instrument 100, FIG. 16 shows the results for four representative photon energies (1.5 keV (curves 710d, 720d, and 730d), 2.5 keV (curves 710c, 720c, and 730c), 6 keV (curves 710b, 720b, and 730b), and 9 keV (curves 710a, 720a, and 730a), including the anticipated contributions of geometric smearing and energy resolution for such photon energies. Specifically, curves for the geometric smearing term ($\delta\theta$ terms) are shown as 710d (1.5 keV), 710c (2.5 keV), 710b (6 keV), and 710a (9 keV). The curves for the energy resolution (a terms) are shown as 730d (1.5 keV), 730c (2.5 keV), 730b (6 keV), and 730a (9 keV). The geometric term is the result of the expected collimation of the X-ray beam 105 to a 0.5 mm diameter and the attendant spot size on the sample, where photons originating from a non-zero extent in sample position $(x_0, y_0, z_0)$ may strike the same detector pixel, blurring the inferred 2θ, and thence d-spacing, values. The energy-resolution term enters into the d-spacing measurement directly through the conversion of energy to wavelength and its application in Bragg's law. Where the highest possible d-spacing resolution is needed, an X-ray source outputting characteristic emission lines may be used so that the detector's energy resolution is not a limiting factor.

In FIG. 16, it is assumed that the sample fills the 0.5 mm diameter beam X-ray beam. At small d-spacing values, the performance of the disclosed third prototype XRD/XRF instrument 100 (see, e.g., FIG. 2c) is comparable to the XRD/XRF instrument 32. However, at larger d-spacing values, the disclosed third prototype XRD/XRF instrument 100 outperforms the XRD/XRF instrument 32. High resolution in measuring d-spacing is essential for accurate mineral identifications and for distinguishing mineral phases within a sample. For samples smaller than the 0.5 mm beam diameter assumed here, the geometric contributions (dotted curves in FIG. 16) to the error budget are much reduced, so that the XRD/XRF instrument 100 resolution is improved, especially at small d-spacing values.

Figure 17A:
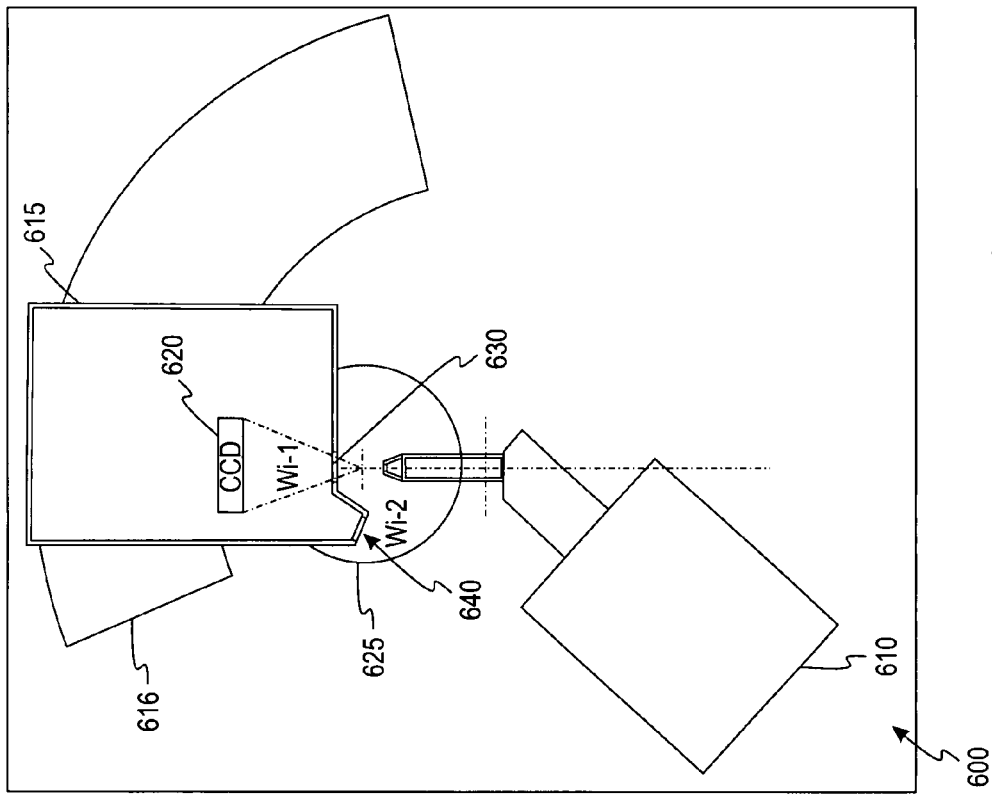
FIGS. 17a-17b depict a dual geometry XRD/XRF instrument in accord with at least some aspects of the present concepts.
Figure 17B:
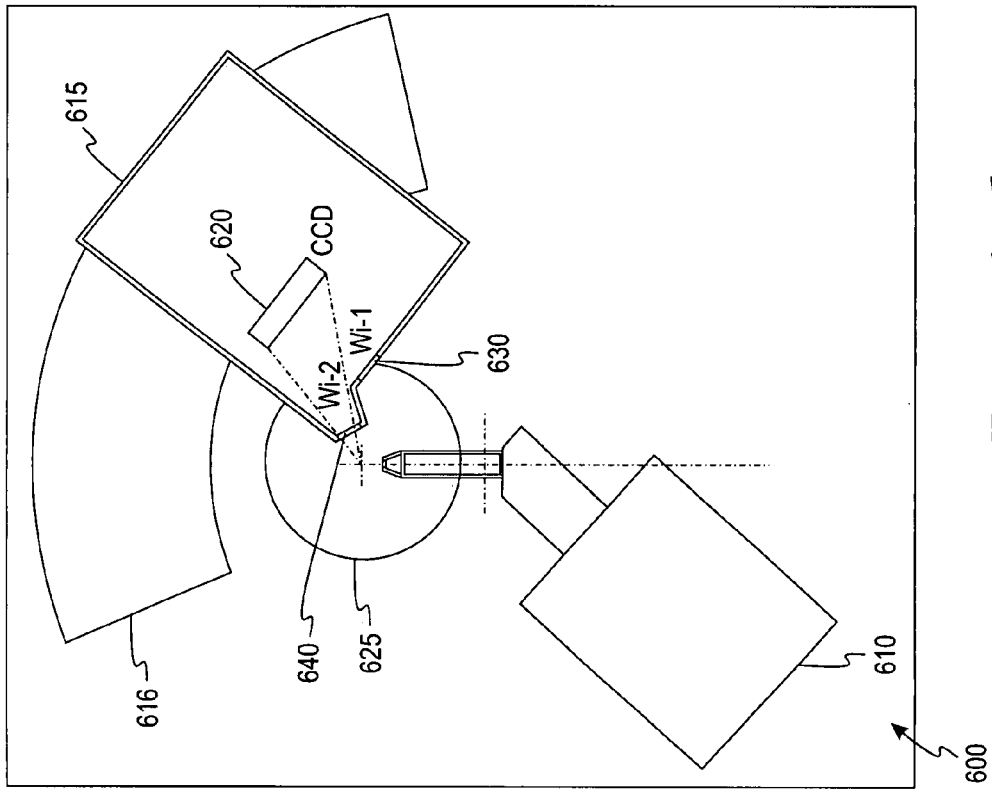

FIGS. 17a-17b depict a dual geometry XRD/XRF instrument 600 in accord with at least some aspects of the present concepts, the instrument comprising an X-ray source 610 and a movable CCD vacuum chamber 615 comprising a CCD 620. In the present example, the X-ray source 610 comprises either X-ray polycapillary optics and/or a collimator in a vacuum enclosure. A Beryllium window (not shown) is provided at an output end of the X-ray source 610. The movable CCD vacuum chamber 615 includes, as illustrated, two windows, a first window 630 and a second window 640. Alternatively, a single window, or more than two windows may be provided. The first window 630 is disposed parallel to the array of CCD 620, whereas the second window 640 is disposed at an angle to the array of CCD 620. When the CCD vacuum chamber 615 is disposed in a first position, as shown in FIG. 17a, the first window 630 is disposed to provide, relative to the X-ray source 610, a transmission geometry. When the CCD vacuum chamber 615 is disposed in a second position, as shown in FIG. 17b, the second window 640 is disposed to provide, relative to the X-ray source 610, a reflection geometry.

In the example of FIGS. 17a-17b, the CCD vacuum chamber 615 is disposed to travel within an arcuate track 616. Alternative mechanisms may also be provided to permit translation and/or rotation of the dual geometry XRD/XRF instrument 600 components relative to one another to permit transition between a transmissive geometry and a reflective geometry. In some aspects, rotation of the CCD vacuum chamber 615 within the track 616 causes a corresponding rotation or movement of the sample support 625. In other aspects, the sample support 625 is fixed.

Aspects of one method in accord with the present concepts, as well as some noted optional variations thereon, is provided below. The acts in the example presented are illustrative, but may be executed in combination with additional non-enumerated acts or in an order other than that presented, to the extent permitted by the data available at any particular juncture.

In an act A110 according to a method for performing X-ray diffraction and X-ray fluorescence in accord with at least some aspects of the present concepts, single-photon events are extracted from the CCD 120 images, producing best estimates of X and Y coordinates, photon energy, and recording start and/or stop time of the exposure. The extraction is done by first subtracting a "dark frame" image, a readout of the pixel contents when the CCD 120 is not illuminated by any radiation, and then systematically searching for local maxima in the resulting background-subtracted image. The digitized values read out for each pixel represent accumulated electric charge, which is proportional to the energy of the photon striking the pixel. The simplest search for localized bright pixels consists of a threshold set sufficiently high so as to avoid fluctuations in the recorded charge due to noise (as recorded, e.g., in the dark frame). A more sophisticated search allows for the possibility that charge deposited by an ionizing photon is distributed into two or more pixels in a tight cluster (e.g., a 3×3 pixel "island"), where a second threshold value may be applied to determine whether an adjacent pixel's brightness is sufficiently high so as to warrant its inclusion in the estimate of total deposited charge for that photon.

The search process then returns X, Y of each pixel (or center of 3×3 island) above threshold, together with the total charge (from a single pixel or summed over the island) and frame readout time. The search process can optionally provide event morphology data for each of these events by describing the distribution of split charge either as a total number of split charge pixels detected per local maximum above threshold or as an encoded expression. The event morphology is used to reject events generated by cosmic rays which is important for space applications. It is also used to optimize the detection efficiency of X-ray photons while maximizing the energy resolution. At this point a selection criterion can be used to only accept events with a given morphology (e.g., single-split or non split events). This basically follows event processing algorithms discussed in Gendreau, K. C., PhD Thesis MIT (1995). From this point forward, the morphology information can be ignored. The result is a filtered event list of X, Y, total charge (energy), and frame readout time. Optionally, it may also be advantageous to accumulate a one-dimensional histogram of energy values as an XRF spectrum to calibrate the detector's gain.

In an act A120, total charge is converted to photon energy. The proportionality relationship, or gain, that links charge to photon energy must be calibrated for any given CCD 120 or other detector. This calibration is typically stable for days or weeks, or longer, provided that the detector's nominal operating temperature is maintained. Gain values may be derived by acquiring data on a calibrator sample (e.g., any substance exhibiting fluorescence lines that span a range of energies, such as Ti Kα through Fe Kβ or others, as seen in the Al 6061 data example, above), or, if the XRD/XRF sample 126 has useful lines, the data may be self-calibrated. In an act A122, a one-dimensional histogram of photon energies is accumulated for detector calibration through the identification of XRF features.

At this point, XRF analysis is possible, but the presence of XRD photons in the dataset may degrade the quality of XRF spectra unless at least some of the following acts are taken.

In an act A130, the photon energy for each photon is converted to wavelength using (Eq. 14)(i.e., $\lambda=hc/E$), as described above.

In an act A140, for a given instrument, the sample position (x0,y0,z0) and incoming beam angle θγ must be measured or calibrated as already described (i.e., either by optical measurement or by using a calibrator sample, such as aluminum). The fixed parameters (θγ, its intercept with the z axis, and y0) apply to all subsequent datasets. One free parameter remains, position along the incoming X-ray beam 105 line, that can be adjusted from sample to sample.

In an act A150, X and Y coordinates for each photon are converted to diffraction angles (θ, φ) for each photon, following geometry already described, assuming the nominal values of calibrated sample position described above or some other position values. Depending on the instrument geometry and detector size and shape, the curvature of the segments of diffraction cones intercepted by the XRD/XRF instrument 100 detector (e.g., CCD 120) may be very small, in which case photon Y information is not especially valuable, and X alone can be used to estimate θ.

In an act A160, using Bragg's law (Eq. 2), a d-spacing value is computed for each detected photon given the wavelength λ determined in act A130, above, and θ from act A150, above. At this point, XRD analysis is possible, but the presence of XRF photons in the dataset may potentially degrade the quality of XRD spectra unless some of the following optional acts are taken. For example, depending on the intended application, an optional act may include accumulating a two-dimensional image binned in energy (E) vs. 2θ. Another optional act A164 may include accumulating a two-dimensional image binned in E vs. d-spacing value. In this way XRF features would be orthogonal to XRD features which may be useful in filtering of the data.

An act A166 includes accumulating a one-dimensional histogram of d-spacing values for instrument calibration. If sample surface roughness or imprecise placement result in inconsistency between the sample's actual position and the assumed, calibrated position (i.e., adjustment of the remaining free parameter in positioning is needed), the d-spacing resolution will be degraded. This may be diagnosed, in act A168, through not-quite-vertical features in an energy vs. d-spacing image, or equivalently in broad diffractogram peaks. The diagnosis may be performed in at least one aspect by an automated search for the correct position performed by "peaking up" the diffractogram by repeating acts A150, A160, A164, and/or A166, until the widths of the diffractogram peaks are minimized and/or their intensities have been maximized. For samples with strong preferred orientation effects, however, this technique may not be applicable.

Once the location of the illuminated spot on the sample has been ascertained and d-spacing values computed for all photons, the act(s) of accumulating a two-dimensional image binned in energy (E) vs. 2θ and/or accumulating a two-dimensional image binned in E vs. d-spacing value are repeated. XRD and XRF phenomena in the dataset may be separated, as demanded by the data, by applying one or more of the techniques already described, such as but not limited to, filtering of horizontal and vertical features in images created in act A164, 2-D Fourier filtering of images created in the acts of accumulating a two-dimensional image binned in energy (E) vs. 2θ and/or accumulating a two-dimensional image binned in E vs. d-spacing value, and/or 2-D simultaneous fitting of XRD and XRF features by matched filtering.

Additionally, following the aforementioned filtering, the method may optionally include accumulating a one-dimensional histogram of d-spacing values for traditional XRD analysis and/or accumulating a one-dimensional histogram of photon energies for traditional XRF analysis. Such histogram should be normalized to account for variations in energy bandwidth and detector area for each of the d-spacing bins into which the histogram is accumulated.

Still further, the method may include, in an act A180, filtering of photon events for one or more d-spacing values, accumulating images in either (X,Y) or (θ, φ) for crystal texture analysis. Features associated with each d-spacing may be plotted in a different color and the individual images combined into a single multi-color image to highlight the relative locations and orientations of the different atomic planes represented by the d-spacing values.

Optionally, additional acts may include generation of analysis products that combine, in various ways, two- or three-dimensional subsets of the four-dimensional data space. For example, time variability of d-spacings may be displayed as an accumulated image, such as is shown by in relation to the example of FIGS. 10a-10c, or similarly for time-varying XRF spectra. Another example would be to create a movie of time-dependent crystal texture by combining texture images, such as that provided by way of example in FIG. 10b, formed for data accumulated in subsets of the full exposure.

Figure 18:
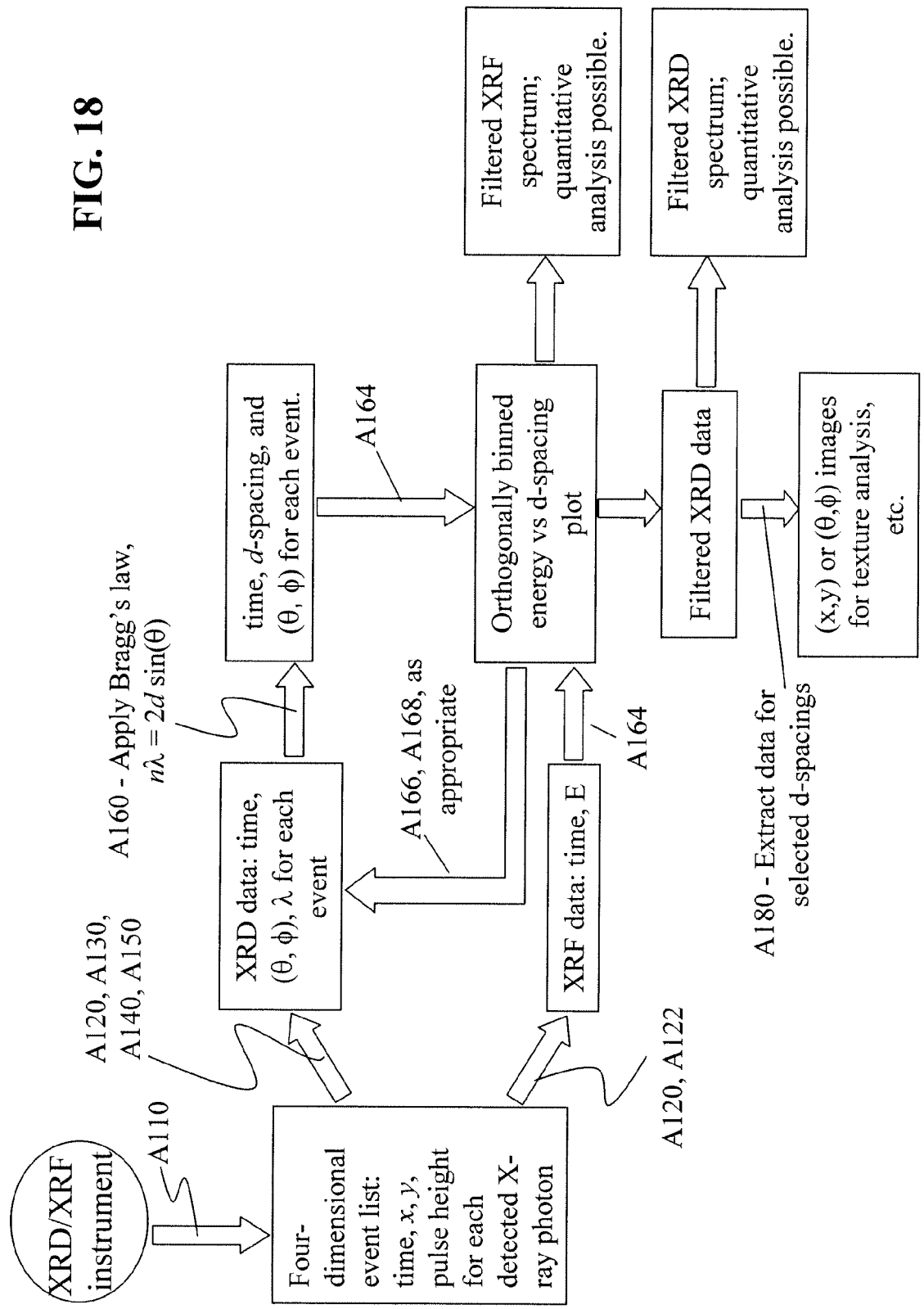
FIG. 18 shows acts in a method in accord with at least some aspects of the present concepts.

The flow chart in FIG. 18 shows one aspect of the data analysis method disclosed above following collection of the XRD/XRDF data in the imaging spectrometer device. The depicted aspect may be used in combination with other intermediate acts, described above.

Each of these embodiments and obvious variations thereof is contemplated as falling within the spirit and scope of the claimed invention, which is set forth in the following claims. As one example, the disclosed XRD/XRF instruments (e.g., 100, 600) may also advantageously comprise a grid (i.e., a reticule) provided between the sample (e.g., 126) and detector (e.g., CCD 120) to enable reticulography. Such grid may, for example, be incorporated into the window 145b. The grid comprises a X-ray absorbing material (e.g., a metal) so that the reticule produces dark lines or shadows in the resulting image. The shadows cast by the grid lines facilitate interpretation of the pattern of spots and splotches (see, e.g., 650, 660 in FIG. 15b) that get reflected from a polycrystalline sample onto the detector. As one additional example, although the present concepts are described in many examples in relation to unprepared samples, there are many applications where prepared or treated samples are highly desirable and the present concepts expressly include utilization of prepared samples in either the reflection geometry or transmission geometry. In still additional alternative embodiments, the present concepts may comprise optical spectroscopy, wherein additional lenses or mirrors, plus an optical diffraction grating, could be added to the system in order to allow the same (X-ray) CCD or a second one to perform the optical reflectance spectral analysis of the sample. Alternatively, a fiber optics spectrometer could be coupled to the system simultaneously observing the sample volume. Still further, the XRD/XRF instrument 100 may comprise a mechanism by which the X-ray beam spot size may be selectively altered to shrink or expand the X-ray beam spot size (e.g., by providing a plurality of selectable collimators, lenses, etc.).

What is claimed is:

1. An X-ray diffraction and X-ray fluorescence instrument for analyzing samples having no sample preparation, comprising:
    a X-ray source configured to output a collimated X-ray beam comprising a continuum spectrum of X-rays to a predetermined coordinate;
    a photon-counting X-ray imaging spectrometer disposed to receive X-ray photons output from an unprepared sample disposed at the predetermined coordinate upon exposure of the unprepared sample to said collimated X-ray beam; and
    a housing defining a vacuum chamber and a sample aperture, the sample aperture comprising an X-ray window disposed therein,
    wherein the X-ray source and the photon-counting X-ray imaging spectrometer are arranged in a reflection geometry relative to the predetermined coordinate,
    wherein the X-ray source is disposed in the vacuum chamber at a first side of the housing and the photon-counting X-ray imaging spectrometer is disposed at a second side of the housing in the vacuum chamber or in another vacuum chamber at the second side of the housing,
    wherein said predetermined coordinate is adjacent an exterior of the X-ray window, and
    wherein said sample aperture comprises a first X-ray window disposed between said X-ray source and said predetermined coordinate outside of the housing and a second X-ray window disposed between said predetermined coordinate outside of the housing and said photon-counting X-ray imaging spectrometer.

2. An X-ray diffraction and X-ray fluorescence instrument according to claim 1, wherein said first X-ray window is inclined to a position substantially perpendicular to said collimated X-ray beam and wherein said second X-ray window is inclined to a position substantially parallel to said photon-counting X-ray imaging spectrometer.

3. An X-ray diffraction and X-ray fluorescence instrument according to claim 2, further comprising:
    an optical lens disposed in said sample aperture;
    an optical charge coupled device disposed within said housing opposite to said optical lens; and
    a partition dividing said housing into a first vacuum chamber and a second vacuum chamber, the X-ray source, optical charge coupled device, and first X-ray window being disposed in said first vacuum chamber and said photon-counting X-ray imaging spectrometer and second X-ray window being disposed in said second vacuum chamber.

4. An X-ray diffraction and X-ray fluorescence instrument according to claim 2, further comprising:
    an optical lens disposed in said sample aperture;
    a movable shutter configured to selectively open and close to respectively transmit or block light output by said optical lens; and
    a mirrored surface disposed to receive light output from said optical lens and to reflect said light onto said photon-counting X-ray imaging spectrometer.

5. An X-ray diffraction and X-ray fluorescence instrument for analyzing samples having no sample preparation, comprising:
    a X-ray source configured to output a collimated X-ray beam comprising a continuum spectrum of X-rays to a predetermined coordinate;
    a photon-counting X-ray imaging spectrometer disposed to receive X-ray photons output from an unprepared sample disposed at the predetermined coordinate upon exposure of the unprepared sample to said collimated X-ray beam;
    a housing defining a vacuum chamber and a sample aperture, the sample aperture comprising an X-ray window disposed therein; and
    an aerosol delivery system, the aerosol delivery system comprising a plurality of aerosol collection spots disposed on a movable substrate, a movable substrate, and a drive system configured to selectively move the aerosol collection spots to said predetermined coordinate,
    wherein the X-ray source and the photon-counting X-ray imaging spectrometer are arranged in a reflection geometry relative to the predetermined coordinate,
    wherein the X-ray source is disposed in the vacuum chamber at a first side of the housing and the photon-counting X-ray imaging spectrometer is disposed in the vacuum chamber at a second side of the housing or in another vacuum chamber at the second side of the housing, and
    wherein said predetermined coordinate is adjacent an exterior of the X-ray window.

6. A method for performing X-ray diffraction and X-ray fluorescence on an unprepared sample, the method comprising the acts of:
    placing an unprepared sample at a predetermined coordinate position of an X-ray diffraction and X-ray fluorescence instrument comprising a broad-spectrum X-ray source and a photon-counting X-ray imaging spectrometer arranged in either a reflection geometry or a transmissive geometry relative to the predetermined coordinate position;

outputting from the broad-spectrum X-ray source a collimated X-ray beam comprising a continuum spectrum of X-rays to the sample;

receiving, at the photon-counting X-ray imaging spectrometer, X-ray photons output from the sample upon exposure of the sample to the collimated X-ray beam;

outputting to a processor data corresponding to each X-ray photon registered by said photon-counting X-ray imaging spectrometer;

preparing an event list; and analyzing, using the event list, at least one of a crystalline texture, crystalline topography, grain size, particle size, or time dependence of crystalline structure of the unprepared sample.

7. A method for performing X-ray diffraction and X-ray fluorescence according to claim 6, wherein the event list comprises an energy of an incident photon and an X-position, a Y-position, or both an X-position and a Y-position at which the incident photon is received by the photon-counting X-ray imaging spectrometer.

8. A method for performing X-ray diffraction and X-ray fluorescence according to claim 7, wherein the event list comprises time.

9. A method for performing X-ray diffraction and X-ray fluorescence according to claim 7, the method further comprising the acts of:

converting X-position and Y-position data to diffraction angle θ and cone azimuth φ for each X-ray photon event sensed by said photon-counting X-ray imaging spectrometer.

10. A method for performing X-ray diffraction and X-ray fluorescence according to claim 9, the method further comprising the act of:

converting event energy to wavelength for each X-ray photon event sensed by said photon-counting X-ray imaging spectrometer.

11. A method for performing X-ray diffraction and X-ray fluorescence according to claim 10, the method further comprising the act of:

calculating the d-spacing for each event.

12. A method for performing X-ray diffraction and X-ray fluorescence according to claim 11, the method further comprising the act of:

plotting the event data in the space of energy versus d-spacing so that X-ray diffraction and X-ray fluorescence features of interest are orthogonal.

13. A method for performing X-ray diffraction and X-ray fluorescence according to claim 12, the method further comprising the acts of:

filtering event data from the event list to provide data for X-ray photons consistent with diffraction from a single d-spacing, and imaging the size and orientation distributions for crystal grains containing said single d-spacing.

14. A method for performing X-ray diffraction and X-ray fluorescence according to claim 6, wherein said time dependence of crystalline structure comprises time dependence of at least one of crystalline texture, crystalline topography, grain size, particle size, d-spacing values, relative diffraction intensities, relative fluorescence intensities, crystal growth, or crystal degradation.

15. An X-ray diffraction and X-ray fluorescence instrument for analyzing an unprepared sample, comprising:

a X-ray source configured to output a collimated X-ray beam comprising a continuum spectrum of X-rays to a predetermined coordinate;

a photon-counting X-ray imaging spectrometer disposed to receive X-rays output from an unprepared sample disposed at the predetermined coordinate upon exposure of the unprepared sample to the collimated X-ray beam, the X-ray source and the photon-counting X-ray imaging spectrometer being arranged in either a reflection geometry or a transmission geometry relative to the predetermined coordinate;

a processor; and a computer-readable medium bearing instructions configured to cause the processor to carry out the steps of preparing an event list from information output to the processor by said photon-counting X-ray imaging spectrometer and analyzing, using the event list, at least one of a crystalline texture, crystalline topography, grain size, particle size, or time dependence of crystalline structure of the unprepared sample.

* * * * *